United States Patent
Nazzaro et al.

(10) Patent No.: US 12,420,022 B2
(45) Date of Patent: Sep. 23, 2025

(54) DRUG DELIVERY DEVICE WITH INDICATOR

(71) Applicant: INSULET CORPORATION, Acton, MA (US)

(72) Inventors: David Nazzaro, Groveland, MA (US); Ian McLaughlin, Groton, MA (US); Daniel Allis, Boxford, MA (US); Simon Kozin, Lexington, MA (US); Maureen McCaffrey, Arlington, MA (US)

(73) Assignee: INSULET CORPORATION, Acton, MA (US)

( * ) Notice: Subject to any disclaimer, the term of this patent is extended or adjusted under 35 U.S.C. 154(b) by 343 days.

(21) Appl. No.: 18/045,739

(22) Filed: Oct. 11, 2022

(65) Prior Publication Data
US 2023/0063696 A1  Mar. 2, 2023

Related U.S. Application Data

(63) Continuation of application No. 16/534,376, filed on Aug. 7, 2019, now Pat. No. 11,497,856, which is a (Continued)

(51) Int. Cl.
*A61M 5/315* (2006.01)
*A61M 5/142* (2006.01)
(Continued)

(52) U.S. Cl.
CPC .... *A61M 5/31568* (2013.01); *A61M 5/14248* (2013.01); *A61M 5/1452* (2013.01);
(Continued)

(58) Field of Classification Search
CPC .......... A61M 5/31568; A61M 5/14248; A61M 5/1452; A61M 5/1454; A61M 5/2033; A61M 5/3155; A61M 2005/14252; A61M 2005/14533; A61M 2005/2073; A61M 2005/31518; A61M 2202/0468; A61M 2205/3306; A61M 2205/3317; A61M 2205/3379; A61M 2205/581; A61M 2205/582; A61M 2205/583; A61M 2205/584; A61M 5/1685; A61M 5/16886; A61M 5/3129; A61M 2205/3389; A61M 5/1684; G01F 11/029; G01F 13/00
See application file for complete search history.

(56) References Cited

U.S. PATENT DOCUMENTS

2005/0255724 A1* 11/2005 Picco ................. H01R 13/6683
439/77
2009/0278875 A1* 11/2009 Holm .................... B05B 7/0408
347/104

* cited by examiner

*Primary Examiner* — Theodore J Stigell
(74) *Attorney, Agent, or Firm* — Goodwin Procter LLP

(57) ABSTRACT

Systems and methods for monitoring an operational state and/or a fill status of a drug container of a drug delivery device are provided. The drug container can hold a liquid drug. A plunger can be positioned within the drug container. A drive system can advance the plunger to expel the liquid drug from the container. A monitoring system can detect a movement and/or a position of the plunger and/or any component coupled to the plunger. The detection can enable determination of an amount of liquid drug that has been expelled and/or an amount of liquid drug remaining in the drug container. Dosing rates, flow rates, and dosage completion can also be determined.

10 Claims, 15 Drawing Sheets

Related U.S. Application Data continuation of application No. 15/676,604, filed on Aug. 14, 2017, now Pat. No. 10,561,797.

(60) Provisional application No. 62/449,845, filed on Jan. 24, 2017, provisional application No. 62/449,849, filed on Jan. 24, 2017, provisional application No. 62/385,749, filed on Sep. 9, 2016, provisional application No. 62/375,026, filed on Aug. 15, 2016, provisional application No. 62/374,881, filed on Aug. 14, 2016.

(51) Int. Cl.
*A61M 5/145* (2006.01)
*A61M 5/20* (2006.01)

(52) U.S. Cl.
CPC ........ *A61M 5/1454* (2013.01); *A61M 5/2033* (2013.01); *A61M 2005/14252* (2013.01); *A61M 2005/14533* (2013.01); *A61M 2005/2073* (2013.01); *A61M 2005/31518* (2013.01); *A61M 5/3155* (2013.01); *A61M 2202/0468* (2013.01); *A61M 2205/3306* (2013.01); *A61M 2205/3317* (2013.01); *A61M 2205/3379* (2013.01); *A61M 2205/581* (2013.01); *A61M 2205/582* (2013.01); *A61M 2205/583* (2013.01); *A61M 2205/584* (2013.01)

DRUG DELIVERY DEVICE WITH INDICATOR

CROSS-REFERENCE TO RELATED APPLICATIONS

This application is a Continuation of U.S. application Ser. No. 16/534,376, filed Aug. 7, 2019, which is a Continuation of U.S. application Ser. No. 15/676,604 (now U.S. Pat. No. 10,561,797), filed Aug. 14, 2017, which claims the benefit of U.S. Provisional Application No. 62/374,881, filed Aug. 14, 2016, U.S. Provisional Application No. 62/375,026, filed Aug. 15, 2016, U.S. Provisional Application No. 62/385,749, filed Sep. 9, 2016, U.S. Provisional Application No. 62/449,845, filed Jan. 24, 2017, and U.S. Provisional Application No. 62/449,849, filed Jan. 24, 2017, all of which are incorporated herein by reference in their entirety.

TECHNICAL FIELD

Embodiments generally relate to medication delivery. More particularly, embodiments relate to wearable drug delivery devices.

BACKGROUND

Many conventional drug delivery devices expel a liquid drug from a drug container for delivery to a patient. These conventional drug delivery devices often fail to inform the patient as to the fill status of the drug container. As a result, the patient is often unaware of how much liquid drug has been provided to the patient, when a desired dose has been completed, and/or how much liquid drug remains in the drug container. Accordingly, there is a need for a monitoring system for use in drug delivery devices that can determine and provide the patient with the fill status of the drug container holding the liquid drug.

DETAILED DESCRIPTION

This disclosure presents various systems, components, and methods related to a wearable drug delivery device and/or monitoring systems for determining a fill status of a drug container of a wearable drug delivery device. Each of the systems, components, and methods disclosed herein provides one or more advantages over conventional systems, components, and methods.

Various embodiments include systems and methods for monitoring an operational state and/or a fill status of a drug container of a drug delivery device. The drug container can hold a liquid drug. A plunger can be positioned within the drug container. A drive system can advance the plunger to expel the liquid drug from the container. A monitoring system can detect a movement and/or a position of the plunger and/or any component coupled to the plunger. The detection can enable determination of an amount of liquid drug that has been expelled and/or an amount of liquid drug remaining in the drug container. Dosing rates, flow rates, and dosage completion can also be determined. Other embodiments are disclosed and described.

Figure 1:
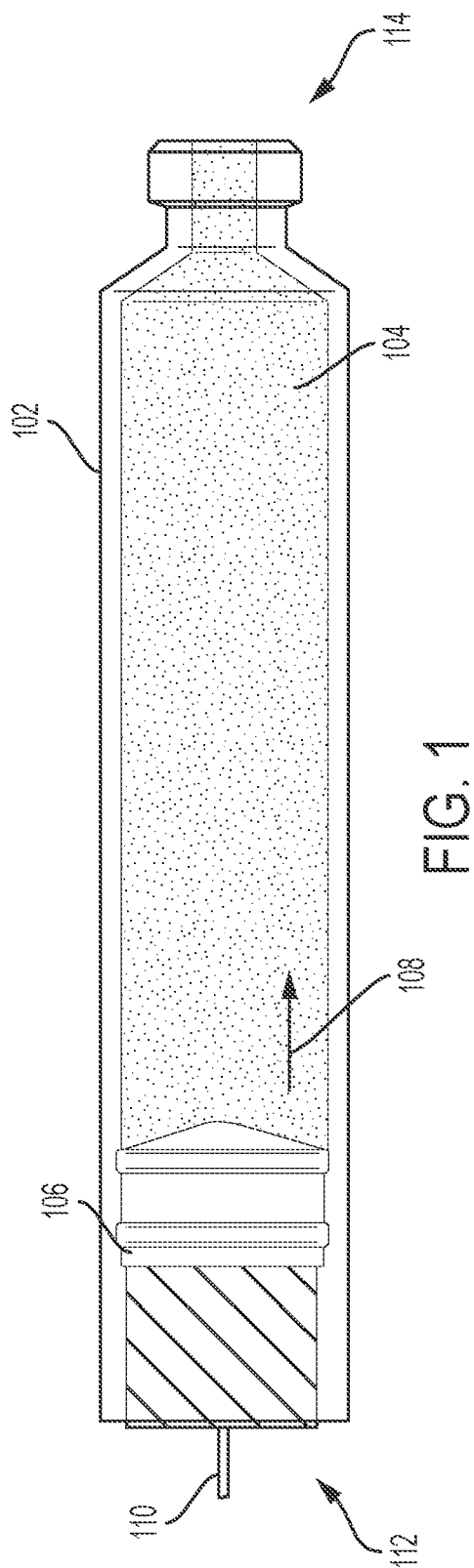
FIG. 1 illustrates an exemplary drug container.

FIG. 1 illustrates an exemplary drug container 102. The drug container 102 can hold or store a liquid drug or other therapeutic agent 104. The drug container 102 can be used within a drug delivery device such as, for example, a wearable drug delivery device. A plunger 106 can be used to expel the liquid drug 104 from the drug container 102 for delivery to a patient. A drive system or mechanism (not shown in FIG. 1 for simplicity) can provide a force on the plunger 106 to drive or advance the plunger 106 in a direction 108 to expel the liquid drug 104 from the drug container 102 (e.g., to advance the plunger 106 from a first position to a second position further into the drug container 102 to expel the liquid drug 104).

A needle conduit 110 can provide the expelled liquid drug 104 to a patient. As shown in FIG. 1, the needle conduit 110 can be coupled to the plunger 106 such that the expelled liquid drug 104 exits from a first end 112 of the drug container 102. Alternatively, the needle conduit 110 can be coupled to a second end 114 of the drug container 102 such that the expelled liquid drug 104 exits from the second end 114 of the drug container 102. The liquid drug 104 can be provided to the patient over one or more doses based on control of the drive mechanism.

The drug container 102 can be made of a variety of materials including, for example, glass or plastic. The drug container 102 is not limited to the shape and size shown in FIG. 1. Instead, the drug container 102 can be of any size or shape. In various embodiments, the drug container 102 can be a prefilled or a Tillable container. In various embodiments, the drug container 102 can be an International Organization for Standardization (ISO) drug container such as, for example, an ISO vial.

Various embodiments described herein provide systems and methods for a patient to readily determine, at any point during use of the drug container 102, how much of the liquid drug 104 is held in the drug container 102, how much of the liquid drug 104 has been expelled from the drug container 104, and/or when a desired dose of the liquid drug 104 has been provided to the patient. Various embodiments described herein provide systems and methods for determining this information based on a position or movement of the plunger 106 and/or based on a position or movement of the drive mechanism used to advance the plunger 106 (or any component of a drug delivery device coupled thereto). Such information allows the patient to confirm proper dose delivery and to verify proper operation of the drug delivery device in which the drug container 102 is used. Without such knowledge, the patient may not be able to confirm whether any liquid drug 104 remains in the drug container 102, how much of the liquid drug 104 has been delivered to the patient, and/or how much of the liquid drug 104 remains to be delivered to the patient. Conventional drug delivery devices do not provide mechanisms for readily determining such information regarding the operational state and/or fill status of drug containers such as the exemplary drug container 102.

Figure 2:
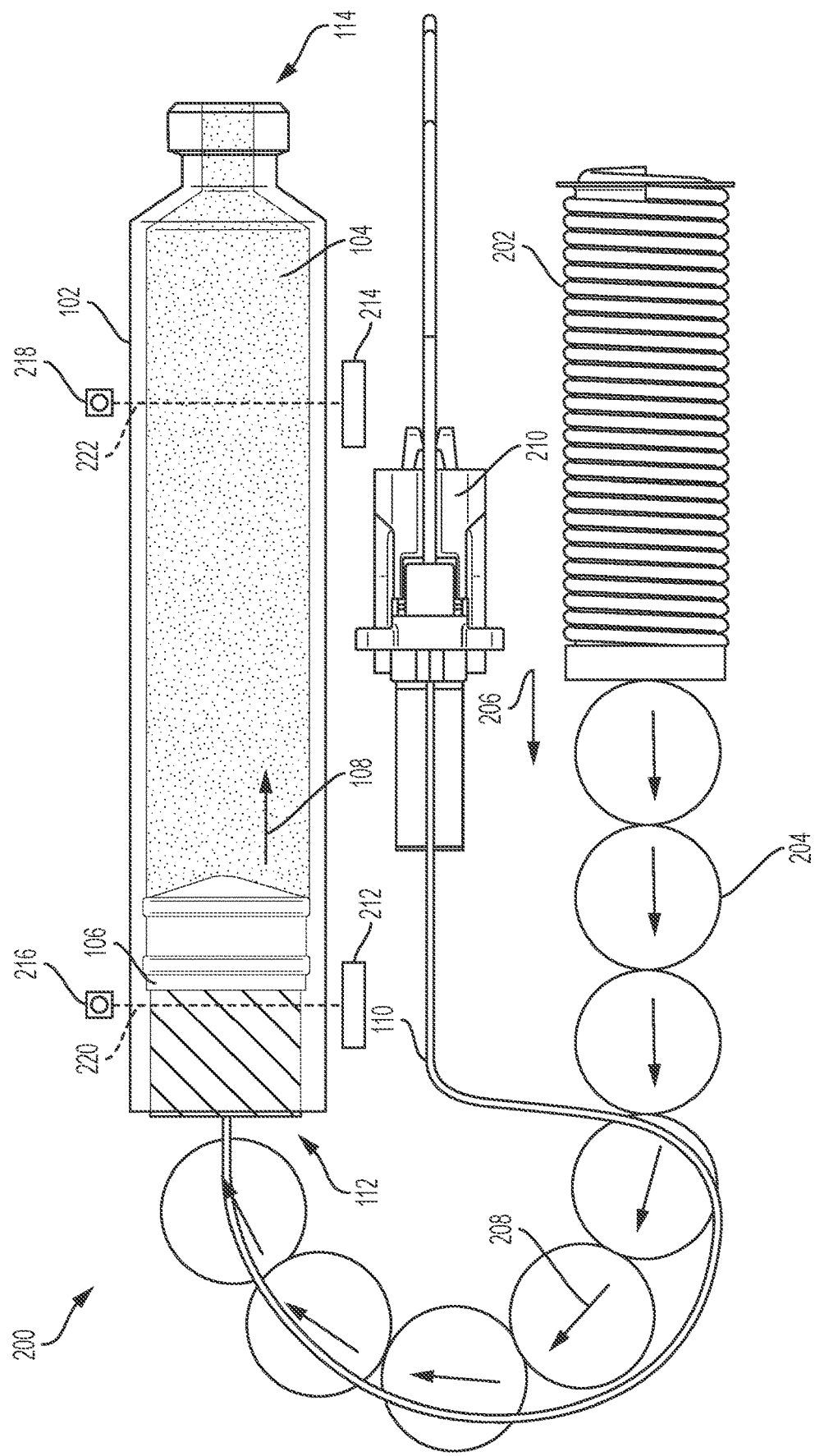
FIG. 2 illustrates a first exemplary drug delivery system.

FIG. 2 illustrates a first exemplary drug delivery system 200. The drug delivery system 200 can include the drug container 102. The drug delivery system 200 can further include a drive mechanism for driving the plunger 106 in the direction 108 to expel the stored liquid drug 104. As an example, the drive mechanism can include a drive spring 202 and a number of spherical elements or components 204 (e.g., a plurality of spherical elements or spheres 204). The spherical elements 204 can be referred to as spherical energy transfer elements or components, or force transfer spheres. As used herein, the spherical elements 204 can be referenced using any of these terms including, for example, spheres 204.

The spherical elements 204 can be positioned within a track (not shown in FIG. 2 for simplicity). The drive spring 202 can expand in a direction 206 to push the spherical elements 204 towards the plunger 106. The force from the drive spring 202 is transferred to the plunger 106 by the spherical elements 204 to drive the plunger 106 in the direction 108, thereby expelling the liquid drug 104 from the drug container 102. A direction of movement of the spherical elements 204 in response to the expansion of the drive spring 202 is shown by indicators 208.

The drug delivery system 200 further includes a needle mechanism 210. The needle mechanism 210 is coupled to the needle conduit 110. Expelled liquid drug 104 is transferred to the needle mechanism 210 by the needle conduit 110, which then provides the expelled liquid drug 104 to the patient. The drug delivery system 200 can be part of a drug delivery system such as, for example, a wearable drug delivery system. The drive mechanism (e.g., the drive spring 202 and the spherical elements 204) of the drug delivery system 200 is exemplary as a variety of different drive mechanisms can be used to expel the liquid drug 104 by advancing the plunger 106 in the direction 108.

The drug delivery system 200 can include a number of mechanisms and/or systems for determining the position of the plunger 106 within the drug container 106. The position of the plunger 106 within the drug container 102 can be used to determine how much liquid drug 104 remains in the drug container 102 and/or how much liquid drug 104 has been expelled from the drug container 102. Based on one or more of these determinations, proper operation of the drug delivery system 200 and dosing of the liquid drug 104 can be verified. The position of the plunger 106 within the drug container 102 can be determined directly and/or can be determined based on positional information of one or more other components of the drug delivery system 200 as further described herein.

As shown in FIG. 2, the drug delivery system 200 can further include one or more sensors such as, for example, a first sensor 212 positioned near the first end 112 of the drug container 102 and a second sensor 214 positioned near the second end 114 of the drug container 102. The sensors 212 and 214 can be used to determine how much liquid drug 104 remains in the drug container 102 and/or how much liquid drug 104 has been expelled from the drug container 102 based on a determination of the position of the plunger 106 within the drug container 102 and/or based on a position of one or more components of a drive mechanism used to advance the plunger 106.

In various embodiments, the sensors 212 and 214 can be Hall effect sensors that can detect the movement and/or position of the plunger 106 and/or the spherical elements 204. For example, as the plunger 106 and the spherical elements 204 move in the direction 108 and into the drug container 102, the sensors 212 and 214 can detect the movement of the plunger 106 and/or the spherical elements 204. As a result, an indication of the position of the plunger 106 within the drug container 102 can be determined, thereby providing a determination of how much liquid drug 104 has been expelled and/or remains in the drug container 102.

In various embodiments, the sensors 212 and 214 can determine how many spherical elements 204 have passed by each respective sensor 212 and 214. Based on a known size of each spherical element 204, a determination on the position of the plunger 106 and/or the rate of movement of the plunger 106 can be made. In various embodiments, the sensors 212 and 214 can determine a position of the plunger 106 along any portion of the drug container 102. In various embodiments, any number of sensors can be used. As Hall effect sensors, the sensors 212 and 214 can measure a varying magnetic field resulting from movement and/or a change in position of the plunger 106 and/or the spherical elements 204.

In various embodiments, the spherical elements 204 can comprise a metallic material. In various embodiments, the spherical elements 204 can include a metallic core that is surrounded by a non-metallic material such as plastic or rubber. In various embodiments, the spherical elements 204 can be made of different types of metal such that the magnetic response of each spherical element 204 as detected by the sensors 212 and 214 differs and can be distinguished. In various embodiments, only certain spherical elements 204 can be comprised of a metallic material that can be detected by one of the sensors 212 and 214. For example, every other spherical element 204 can comprise a metallic material that can be detected by one of the sensors 212 and 214. Based on a predetermined arrangement of the spherical elements 204, as the drive mechanism advances the plunger 106, positional information of the plunger 106 can be determined.

In various embodiments, a portion of the plunger 106 can comprise a metallic material such that the sensors 212 and 214 can detect the position of the plunger 106 within the drug container 102. In various embodiments, any number of sensors can be used and can be arranged along the drug container 102. The detection of the position of the plunger 106 is not limited to the drive mechanism shown in FIG. 2. In general, the drug delivery system 200 can include any drive system configured such that the sensors 212 and 214 can be used to detect the position of the plunger 106 based on detection of the plunger 106 position directly and/or detecting a position of any portion of a drive system used to advance the plunger 106 in the direction 108. For example, the drive system can include a push rod, one or more cylinders, and/or one or more springs for driving movement of the plunger 106 with the sensors 212 and 214 operating to detect the position or movement of any of these components. Any of the techniques described herein for determining the fill status of a drug container 102 and/or a position or movement of the plunger 106, either directly or indirectly, are applicable to any such drive mechanism, such as those described above, as will be appreciated by a person of ordinary skill in the art.

In general, as Hall effect sensors, the sensors 212 and 214 can detect and measure a magnetic field as it varies as the plunger 102 and the spherical elements 204 are advanced in the direction 108. The sensors 212 and 214 can each generate signals indicative of the measured magnetic field. A controller (not shown in FIG. 2) can be coupled to the sensors 212 and 214 and can receive signals generated by the sensors 212 and 214. The controller can detect characteristic waveforms corresponding to the plunger 102 and/or the spherical elements 204 (or any other component of a drive system) so as to track a movement or position of the plunger and/or the spherical elements 204 and/or count a number spherical elements 204 that pass each of the sensors 212 and 214. In general, based on signals generated by the sensors 212 and 214, the controller can determine a position of the plunger 106 within the drug container 102. In this way, the controller can determine a fill status of the drug container 102 and/or the beginning or end of the stroke of the plunger 106.

In various embodiments, the sensors 212 and 214 can be optical sensors. In various embodiments, the sensors 212 and 214 can detect the position of the plunger 106 based on optical detection. As an example, the drug delivery system 200 can include a first light emitting device or light source 216 and a second light emitting device or light source 218. A first light beam 220 emitted by the first light emitting device 216 can be detected by the first sensor 212 and a second light beam 222 emitted by the second light emitting device 218 can be detected by the second sensor 214. The first and second light beams 220 and 222 emitted from the first and second light emitting devices 216 and 218, respectively, can be interrupted or blocked by the plunger 106 and/or the spherical elements 204 (or any other drive mechanism component) as the drive mechanism drives the plunger 106 in the direction 108. As an example, the sensors 212 and 214 and corresponding light sources 216 and 218 can positioned off center from a central axis of the spherical elements 204 such that, as the spherical elements 204 are advanced, reception of the light beams 220 and 222 by the sensors 212 and 214, respectively, can be occasionally interrupted.

The sensors 212 and 214 can detect these interruptions in detection of the first and second light beams 220 and 222, respectively, and can use the detections to determine the position of the plunger 106. In various embodiments, the sensors 212 and 214 can count the number of spherical elements 204 that have passed into the drug container 102 by counting a number of interruptions, thereby providing an estimate of the position of the plunger 106. In various embodiments, the position of the plunger 106 can be determined as the plunger 106 itself interrupts light detection by a number of sensors positioned along the drug container 102.

In various other embodiments, the sensors 212 and 214 themselves can emit light and can detect reflected light from any portion of the plunger 106 and/or any portion of the drive mechanism (e.g., the spherical elements 204). In various embodiments, the plunger 106 and/or the spherical elements 204 can be coated with different light absorbing and/or reflecting materials, such that each element reflects and/or absorbs light differently. Based on the light reflected by the elements, the sensors 212 and 214 can detect the advancement of the plunger 106 and/or the spherical elements 204 and therefore the position of the plunger 106.

In general, the sensors 212 and 214 and operation thereof to detect the position of the plunger 106 can be independent of the drive mechanism used to advance the plunger 106. As noted above, the position of the plunger 106 can be determined based on sensors 212 and 214 as Hall effect sensors or optical sensors. The sensors 212 and 214 can be electrically coupled to a controller (not shown in FIG. 2) that can determine the position of the plunger 106 based on information collected or determined by the sensors 212 and 214. The sensors 212 and 214 can form a portion of a monitoring system for the drug delivery system 200 that can determine an operational state or fill status of the drug container 102 such that how much liquid drug 104 has been expelled or remains in the drug container 102 can be determined. The monitoring system of which the sensors 212 and 214 can be a part can aid this determination based on detection of a position and/or movement of the plunger 106 and/or any component of a drive system used to advance the plunger 106.

Figure 3:
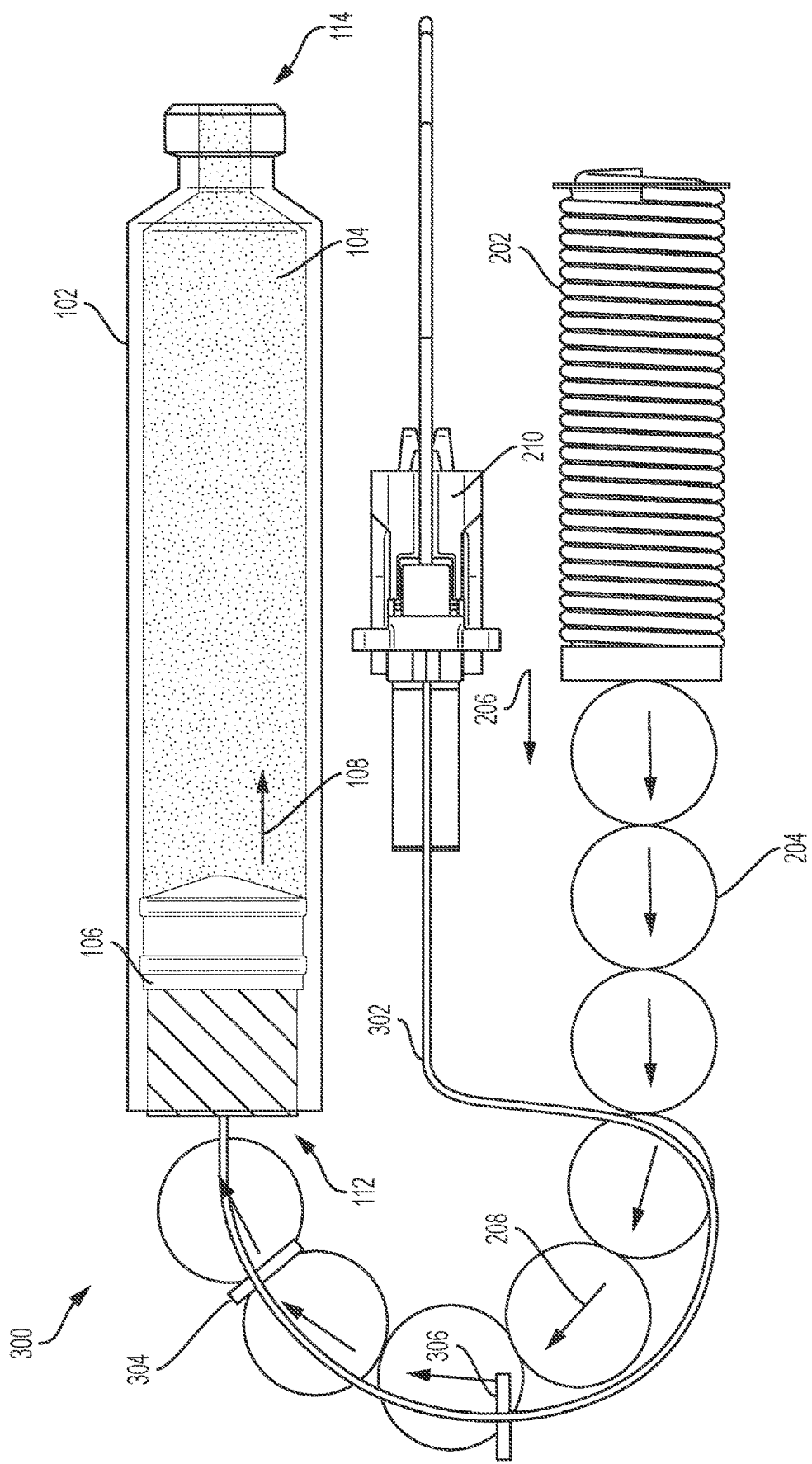
FIG. 3 illustrates a second exemplary drug delivery system.

FIG. 3 illustrates a second exemplary drug delivery system 300. The drug delivery system 300 can operate in a similar manner with respect to the drug delivery system 200 to expel the liquid drug 104 from the drug container 102 for delivery to the patient. As shown in FIG. 3, the drug delivery system 300 can include a needle conduit 302 and one or more sensors such as, for example, a first sensor 304 and a second sensor 306. The needle conduit 302 can be an encoded needle conduit as described further herein. In various embodiments, the needle conduit 302 can be encoded along its length in a manner to reveal or indicate positional information of the needle conduit 302 as it moves with the plunger 106 as the plunger 106 is advanced into the drug container 102. The first and second sensors 304 and 306 can detect the encoded positional information of the needle conduit 302 to thereby determine the position of the plunger 106.

In various embodiments, the needle conduit 302 can comprise a metal tubing that is coated in various regions with a non-conductive coating. The sensors 304 and 306 can detect the conductive and non-conductive regions of the needle conduit 302. As the needle conduit 302 advances and passes over the sensors 304 and 306 (e.g., making electrical contact with the sensors 304 and 306), the sensors 304 and 306 can distinguish the conductive and non-conductive regions. The sensors 304 and 306 can be coupled to a controller (not shown in FIG. 3) that tracks the count and/or length of these different regions. Based on a predetermined arrangement of the conductive and non-conductive regions of the encoded needle conduit 302—for example, based on the number of different regions and their lengths or sizes—the controller can determine the position of the plunger 106. Further, the controller can determine a rate of movement of the plunger 106. This information can then be used to determine a fill status of the drug container 103 and a dosing status of the liquid drug 104.

The sensors 304 and 306 can be arranged to be coupled to the needle conduit 302 as the needle conduit 302 advances in response to movement of the plunger 106. The sensors 304 and 306 can further be arranged to not interfere with the drive mechanism (e.g., the spherical elements 204). Further, any number of sensors can be arranged to be coupled to the needle conduit 302.

Figure 4:
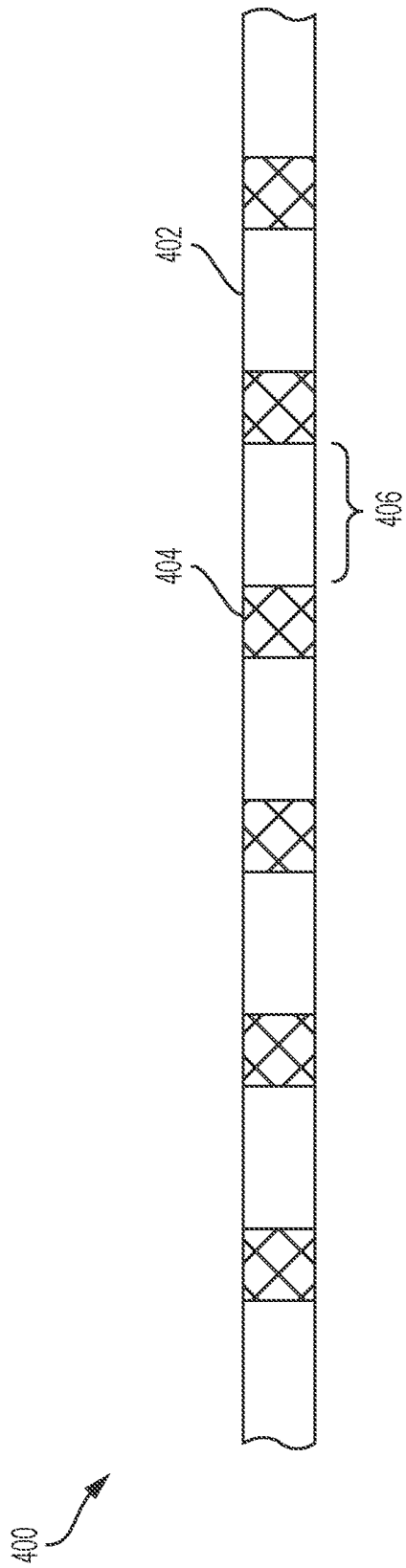
FIG. 4 illustrates a portion of an exemplary encoded needle conduit.

FIG. 4 illustrates a portion of an exemplary encoded needle conduit 400. The encoded needle conduit 400 can represent the needle conduit 302 depicted in FIG. 3. As shown in FIG. 4, the encoded needle conduit 400 includes conductive regions 402 and non-conductive regions 404.

The conductive regions 404 can be spaced apart by a distance 406. The sizes of the conductive regions 402 and the non-conductive regions 404 (and therefore the distance 406) of the encoded needle conduit 400 can be uniform but is not so limited. In general, any known or predetermined arrangement of the conductive regions 402 and the non-conductive regions 404 can be used to determine the position of the plunger 106. The conductive regions 402 can exhibit substantially the same or different levels of conductivity that can also be used to determine a position and/or a movement of the plunger 106.

As the sensors 304 and 306 detect and/or come into electrical contact with the conductive regions 402 and/or the non-conductive regions 404, the sensors 304 and 306 can distinguish the conductive regions 402 from the non-conductive regions 404 and can determine what portion of the encoded needle conduit 400 is passing over each of the sensors 304 and 306. The sensors 304 and 306 can further detect the rate of movement of the encoded needle conduit 400 and can estimate a position and/or movement of the plunger 106 relative to the position and/or movement of the encoded needle conduit 400.

In various embodiments, the sensors 304 and 306 can be optical sensors. In various embodiments, the needle conduit 302 can marked in a manner for the sensors 304 and 306 to detect positional information of the needle conduit 302. For example, the needle conduit 302 can be laser marked or etched so as to distinguish different segments of the needle conduit 302 that the sensors 304 and 306 can identify. As another example, the needle conduit 302 can be marked with one or more bar codes along one or more portions of the needle conduit 302 so as to distinguish different segments of the needle conduit 302 that the sensors 304 and 306 can identify. As the marked needle conduit 302 passes over the sensors 304 and 306, the sensors 304 and 306 (e.g., as barcode readers) can optically detect what portion of the encoded needle conduit 302 is passing each of the sensors 304 and 306, enabling the position of the plunger 106 to be determined.

The sensors 304 and 306 and the encoded needle conduit 302 can form a portion of a monitoring system for the drug delivery system 300 that can determine an operational state and/or fill status of the drug container 102 such that how much liquid drug 104 has been expelled or remains in the drug container 102 can be determined. The monitoring system of which the sensors 304 and 306 and the needle conduit 302 can be a part can aid this determination based on detection of a position and/or movement of the needle conduit 302 that is coupled to the plunger 106.

In various embodiments, a window or viewing area can be positioned on a drug delivery device to enable the patient to view a portion of a drug container and/or a portion of the drive mechanism to enable the patient to determine the fill status of the drug container and/or the operational status of the drug container. The window can be part of any drug delivery device or drug delivery system described herein and can be used in conjunction with any mechanism described herein for determining the fill status of a drug container.

Figure 5:
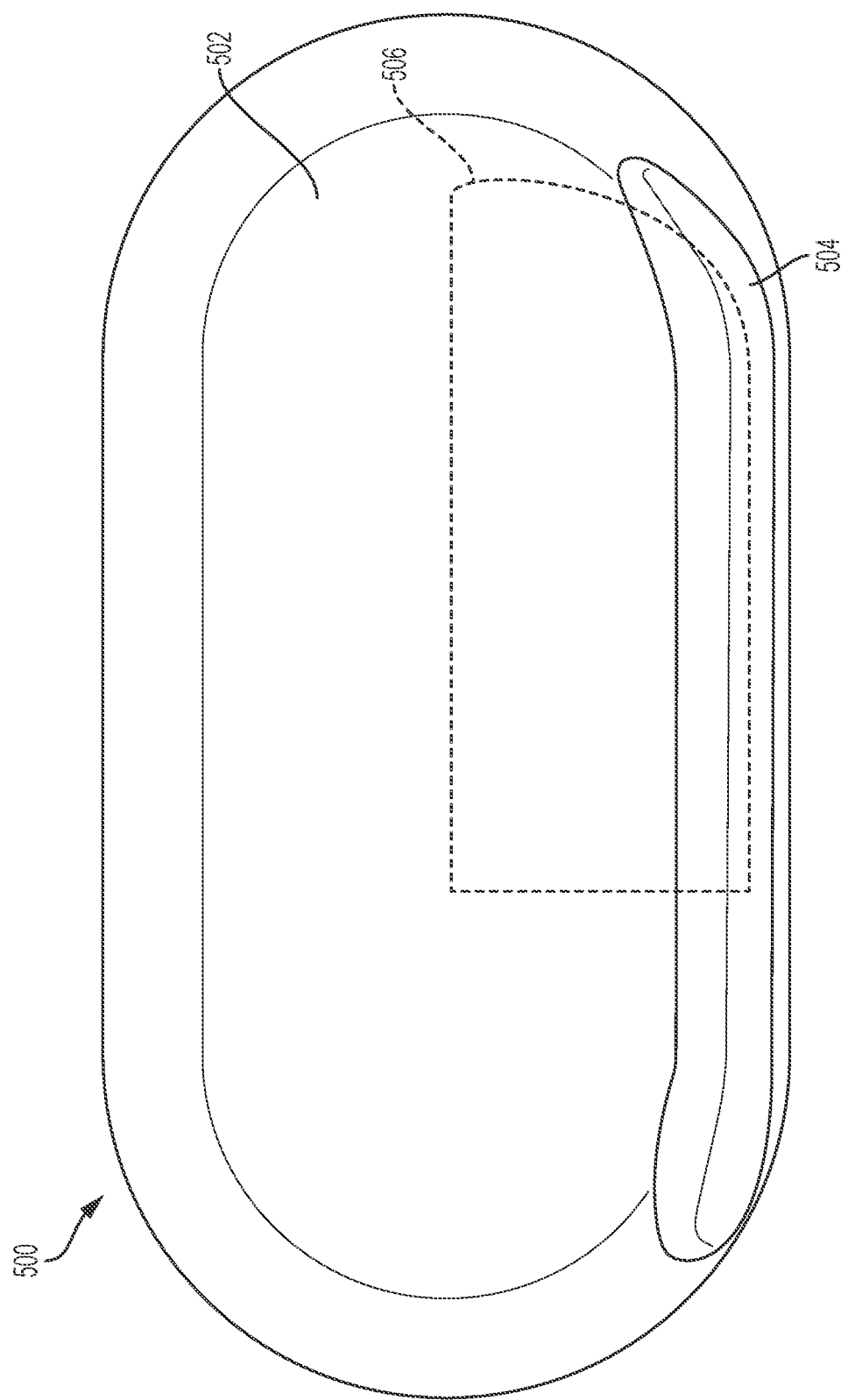
FIG. 5 illustrates a top view of an exemplary drug delivery device.

FIG. 5 illustrates a top view of an exemplary drug delivery device 500. As shown in FIG. 5, the drug delivery device 500 can include an upper portion 502. The upper portion 502 can be a top portion or a cover of the drug delivery device 500. The drug delivery device 500 can further include a raised portion 504. The raised portion 504 can be elongated and can run along a side of the drug delivery device 500. A container for holding a liquid drug can be approximately positioned under the raised portion 504 such that the raised portion 504 accommodates the size and positioning of the liquid drug container within the drug delivery device 500. As an example, a container such as the drug container 102 can be positioned under the raised portion 504. Any drug delivery system described herein can be positioned within the drug delivery device 500.

The upper portion 502 of the drug delivery device 500 can include a window or viewing area 506. The window 506, for example, can be made of plastic and can be transparent. The window 506 can be of any size and shape and can be positioned on any portion of the drug delivery device 500. The window 506 can allow a patient to view internal components of the drug delivery device 500 such as, for example, a portion of the drug container positioned within the drug delivery device 500 (e.g., under a portion of the raised portion 504) and/or a portion of the drive mechanism coupled to the drug container. The patient can determine how much liquid drug is in an internal drug container by viewing the drug container through the window 506.

In various embodiments, the spherical elements 204 can be differently colored to indicate a dosing status of the liquid drug 104 (and/or a fill status of the drug container 102). For example, the window 506 can be positioned on the upper portion 502 to allow a user to view all or a portion of the drug container 102. The spherical elements 204 can be driven into the drug container 102 as the spherical elements 204 push on the plunger 106. The user can view the spherical elements 204 enter the drug cartridge 102. The spherical elements 204 can be colored differently (or marked or otherwise visually distinguished) in a predetermined sequence or manner to indicate how much of the liquid drug 104 has been expelled from the drug container 102. The marking or coloring of the spherical elements 204 can be adjusted based on the size of a dose of the liquid drug 104 or an entire amount of liquid drug 104 stored in the drug container 102.

For example, an initial set of spherical elements 204 can be marked in a first manner (e.g., by a first color such as green) to indicate an initial expulsion of the liquid drug 104 when the initial set of spherical elements 204 enter the drug container 102 and can be viewed. An intermediate set of spherical elements 204 can be marked in a second manner (e.g., by a second color such as yellow) to indicate an intermediate expulsion of the liquid drug 104 when the intermediate set of spherical elements 204 enter the drug container 102 and can also be viewed. A final set or final spherical element 204 can be marked in a third manner (e.g., by a third color such as red) to indicate a final expulsion of the liquid drug 104 (e.g., end of dose or completion of dose) when the final set or final spherical element 204 enters the drug container 102 and is visible to the user through the window 506.

As will be appreciated by a person of ordinary skill in the art, any type of marking (e.g., coloring) including text or other symbols and any number of groupings and corresponding distinctions (e.g., number of intervals or gradations) can be used to indicate the dosing status or the fill status of the drug container 102 based on the spherical elements 204 entering the drug container 102. Further, as will be appreciate by a person of ordinary skill in the art, any drive mechanism component used to drive the plunger 106—including, for example, a push rod, one or more cylinders, and/or one or more springs—that enters the drug container 102 can be marked in a manner to indicate dosing status or fill status of the drug container 102 based on the extent to which any portion of the drive mechanism component has entered the drug container 102. Further, any marking or coloring of any component of the drive system can be based on a predetermined dose size and/or a total amount of the liquid drug 104 stored in the drug container 102. In various embodiments, the drive mechanism component or components can be marked to simply indicate a completion of a dose—for example, when a red colored portion of the drive mechanism is visible in the drug container 102, dose completion can be indicated.

In various embodiments, a sensor can be positioned adjacent to the drug container 102 that can track or a count a number of the spherical elements 204 or other drive system components that enter the drug container 102 to provide an indication of dosing status or fill status of the drug container 102. For example, with reference to FIG. 2, a sensor can be positioned adjacent to a first end 112 of the drug container 102. The sensor can mechanically or can electromechanically count a number of the spherical elements 204 that pass the sensor as the spherical elements 204 enter the drug container 102. In various embodiments, the sensor can be a switch that is triggered each time a spherical element 204 passes the sensor. The switch could be implemented as a mechanical switch or can be implemented as an electromechanical switch. As part of an electromechanical system, the sensor can be coupled to a display (e.g., an LED display) for indicating dosing status or fill status of the drug container 102. A mechanical implementation can include a wheel that has different colors or symbols indicating dose status that can be rotated by the passing of the spherical elements 204.

Figure 6:
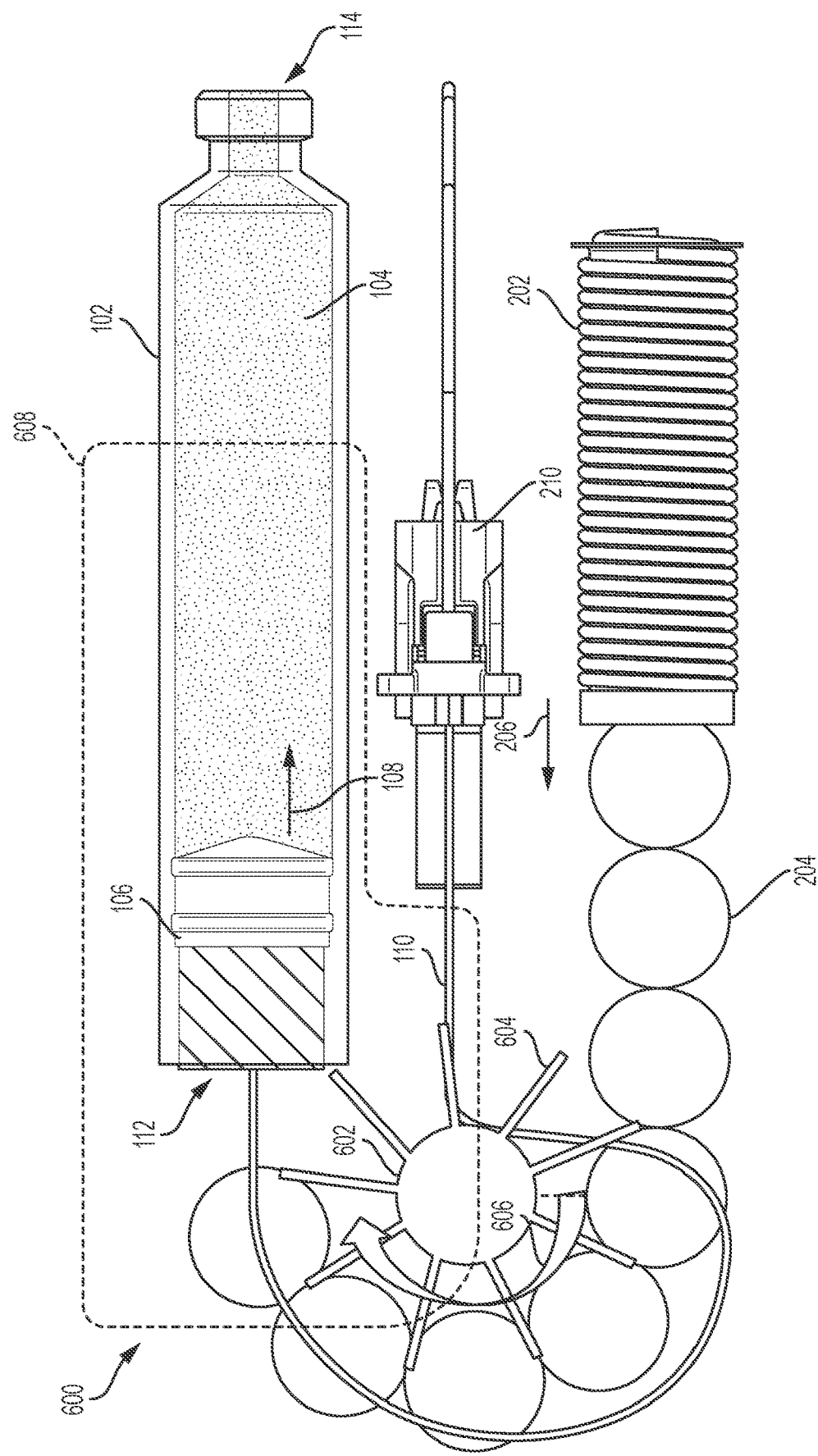
FIG. 6 illustrates a third exemplary drug delivery system.

FIG. 6 illustrates a third exemplary drug delivery system 600. The drug delivery system 600 can include features of the drug delivery system 200 and can further include a dosing wheel 602. The dosing wheel 602 can include a number of arms or spokes 604 that radially extend from a hub. The dosing wheel 602 can have any number of arms 604. One or more of the arms 604 can be positioned between adjacent spheres 204. The dosing wheel 602 can rotate in a direction 606 as shown about an axis of the dosing wheel 602 to move the spheres 204 forward toward the drug container 102. The drive spring 202 can provide the force to move the spheres 204 as regulated by the dosing wheel 602. That is, the dosing wheel 602 can impede forward movement of the spheres 204 until the dosing wheel 602 rotates a desired amount in the direction 606. The drug delivery device 600 can operate as a single dose or multiple dose drug delivery device by regulating movement of the spheres 204.

In various embodiments, movement of the dosing wheel 602 can trigger a counter or other device to track rotational movement of the dosing wheel 602. For example, a counter coupled to the dosing wheel 602 can track the number of times the dosing wheel 602 has advanced a single sphere 204 forward. In doing so, the counter can provide the patient with an indication of how much liquid drug 104 has been delivered. In various embodiments, the counter can be coupled to the dosing wheel 602 mechanically. For example, the counter can be coupled to a gear system of the dosing wheel 602 and/or can be arranged to be triggered by contact with the arms 604 as the arms 604 rotate. In various embodiments, the dosing wheel 602 can be coupled to a controller (not shown in FIG. 6) that can track the rotational movement of the dosing wheel 602 and can provide an indication of the filling status of the drug container 102 to the patient.

In various embodiments, the drug delivery system 600 can be housed within a device (e.g., the drug delivery device 500) having a window 608 (shown in phantom). The window 608 can enable a user to view a portion of the dosing wheel 602, a portion of the drug container 102, and/or a position of the plunger 106 within the drug container 102. In various embodiments, the window 608 can be positioned over a portion of the dosing wheel 602 to allow the patient to view the rotation of the arms 604. In various embodiments, the arms 604 of the dosing wheel 602 can be differently colored (e.g., color coded) or otherwise distinguished visually (e.g., by text or other symbols or markings) to indicate how far the dosing wheel 602 has rotated, thereby providing an indication of how far the plunger 106 has advanced into the drug container 102.

Figure 7:
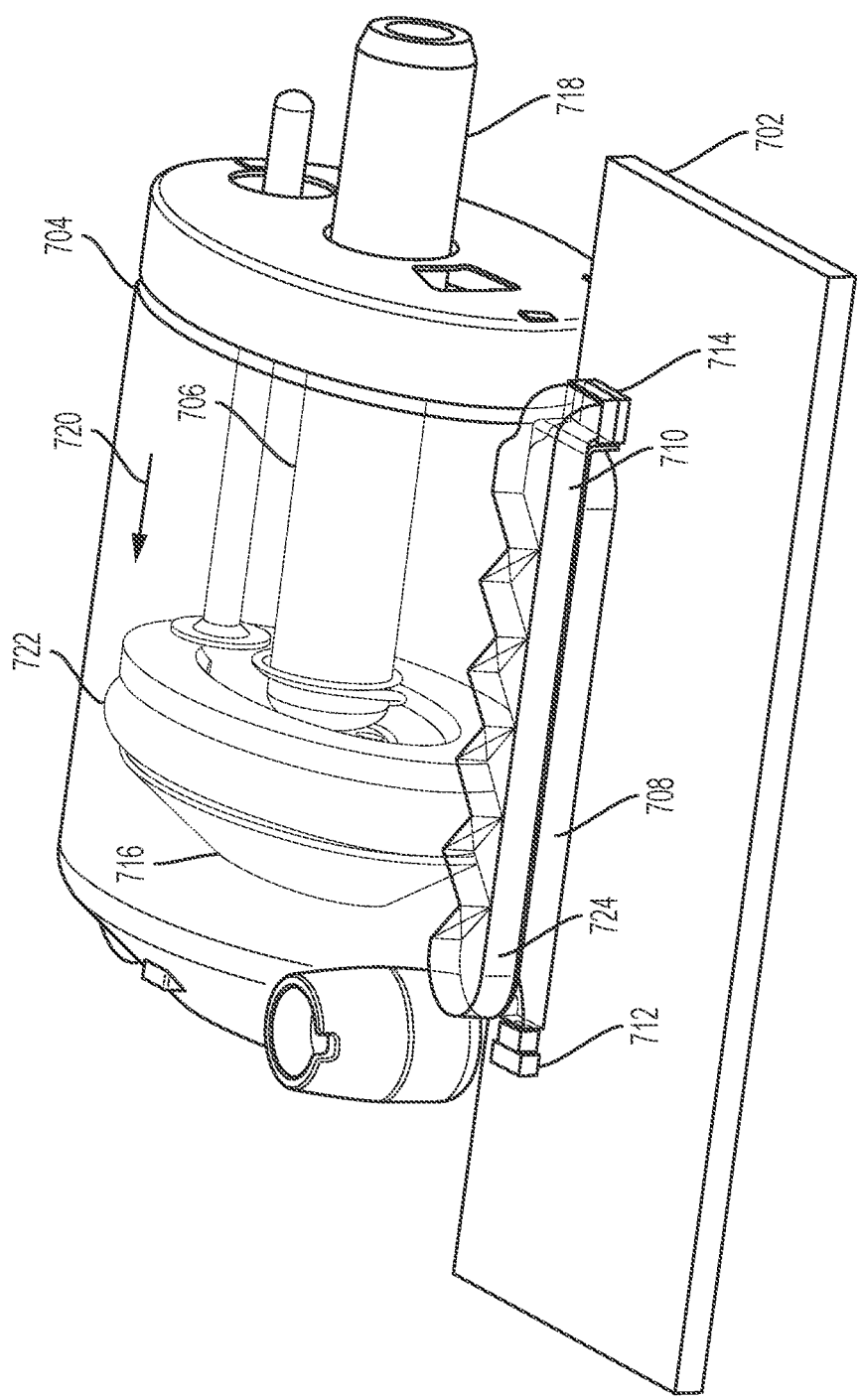
FIG. 7 illustrates an optical monitoring system.

FIG. 7 illustrates an optical monitoring system 700 for determining the amount of liquid drug stored in a drug container. As shown in FIG. 7, the optical monitoring system 700 includes a printed circuit board (PCB) 702, a drug container 704, a plunger 706, an attenuating light pipe 708, a non-attenuating light pipe 710, a light emitting source 712, and a detector 714.

The drug container 704 can be positioned adjacent to the PCB 102 and can store a liquid drug or other therapeutic agent. The plunger 706 can be positioned within the drug container 704 and can be used to expel the liquid drug from the drug container 704. The plunger 706 can include a head portion 716 and a base or rod portion 718. The rod 718 can extend out of the drug container 704. A drive mechanism (not shown in FIG. 7) can drive the plunger 706 in a direction 720 to expel stored liquid drug from the drug container 704 for delivery to a patient. The plunger can include a reflective portion 722 such as, for example, a reflective O-ring. The reflective O-ring 722 can be positioned on the head portion 716 of the plunger 706. The reflective portion 722 can reflect light that is incident on the plunger 706.

The light emitting source 712 can be a light emitting diode (LED). The detector 714 can be a photodiode. The non-attenuating light pipe 710 can be positioned on top of the attenuating light pipe 708. The attenuating light pipe 708 can be coupled to the light emitting source 712. The light pipes 708 and 710 can be positioned adjacent to the drug container 704. The attenuating light pipe 708 can be configured to emit light from the light emitting source 712 out of the attenuating light pipe 708. The non-attenuating light pipe 710 can be configured to receive light reflected off the reflective portion 722 and to provide the received light to the detector 714. In various embodiments, the attenuating light pipe 708 can be configured to emit light from the attenuating light pipe at a first angle and the non-attenuating light pipe 710 can be configured to receive light from a second angle that is orthogonal to the first angle. The first and second angles are not limited to being orthogonal to one another. In various embodiments, the first and second angles can be acute or obtuse to one another. In various embodiments, the first and second angles can be oriented to adjust the effective intensity of light energy received by the non-attenuating light pipe 710.

The light emitting source 712 can emit light and provide emitted light into the attenuating light source 708. Light provided to the attenuating light pipe 708 from the light emitting source 712 can then be emitted from the attenuating light pipe 708. The attenuating light pipe 708 can be configured to attenuate the light it receives along the length of the attenuating light pipe 708. Specifically, light emitted from the attenuating light pipe 708 that is further from the light emitting source 712 can be attenuated more than light emitted from the attenuating light pipe 708 that is closer to the light emitting source 712. The non-attenuating light pipe 710 is not specifically configured to attenuate light within the non-attenuating light pipe 710. The non-attenuating light pipe 710 can be coupled to the detector 714 such that light received by the non-attenuating light pipe 710 can be provided to the detector 714.

A reflector 724 can be positioned between the attenuating light pipe 708 and the non-attenuating light pipe 710. In various embodiments, the reflector 724 can be positioned over a top surface of the attenuating light pipe 708 and below a button surface of the non-attenuating light pipe 710. The reflector 724 can prevent light from passing between the attenuating light pipe 708 and the non-attenuating light pipe 710 (e.g., directly passing). The reflector 714 can be a film or painted component positioned between the attenuating light pipe 708 and the non-attenuating light pipe 710 or provided on a surface of one of the attenuating light pipe 708 and the non-attenuating light pipe 710.

The light emitting source 712 can provide a stable source of light to the attenuating light pipe 708. The light provided to the attenuating light pipe 708 can be emitted from the attenuating light pipe 708 along the length of the attenuating light pipe 708. The emitted light can illuminate the internal portion of the drug container 704 and the plunger 706. A portion of the light that enters the drug container 704 from the attenuating light pipe 708 can be reflected by the reflective portion 722. This reflected light can then be received by the non-attenuating light pipe 710. The light received by the non-attenuating light pipe 710 can then be provided to the detector 714.

The detector 714 can determine an intensity of the light received or provided to the detector 714. The detector 714 can generate a signal based on the intensity of light received. As the plunger 706 moves along the length of the drug container 704, light of different intensities will be reflected off of the reflective portion 722 of the plunger 706. In general, the intensity of the reflected light can vary linearly with the movement of the plunger 706 based on the characteristics of the attenuating light pipe 708. The detector 714 can detect the changing intensity of the received light that is reflected off the reflective portion 722. Based on the intensity of the received light, the detector 714 can determine a position of the reflective portion 722 and therefore the plunger 706 within the drug container 704. In turn, a determination of how much liquid drug remains in the drug container can be made. Further, the measured signals from the detector 714 can be used to determine a rate of movement of the plunger 706. Depending on the movement of the plunger 706 relative to the light emitting source 712, the intensity of the light detected by the detector 714 can increase or decrease as the plunger 706 advances further into the drug container 704.

As shown in FIG. 7, the optical monitoring system 700 is arranged to provide relatively lower attenuated light to the detector 714 when the plunger 706 is positioned closer to the light source 712 (and to provide relatively higher attenuated light to the detector 714 when the plunger 706 is positioned closer to the detector 714). As a result, the intensity of the light provided to the detector 714 will increase as the plunger 706 is advanced to expel additional liquid drug from the drug container 704. The optical monitoring system 700 is not limited to this arrangement. In various embodiments, the optical monitoring system 700 can be arranged such that the intensity of the light provided to the detector 714 will decrease as the plunger 706 is advanced to expel additional liquid drug from the drug container 704. Overall, the optical monitoring system 700 can be arranged to provide light to the detector 714 that varies in intensity based on movement of the plunger 706 (e.g., advancement of the plunger 706 to expel the liquid drug). A controller (not shown in FIG. 7) coupled to the detector 714 can detect a position of the plunger 706 based on the signals generated by the detector 714 that indicate the intensity of light received by the detector 714.

The optical monitoring system 700 can be used with any drug container storing a liquid drug that is expelled by any linear translating component having a reflective portion. For example, the drug container 102 and the plunger 106 can be used in the optical monitoring system 700. Further, any portion of the plunger 706 can be reflective including any component coupled to the plunger 706 that moves with the plunger 706 to expel a stored liquid drug. The drug container 704 used with the optical monitoring system can be a transparent container (or a portion thereof can be transparent).

The optical monitoring system 700 can use any type of radiation emitting/detecting pair such as, for example, an infrared, a visible light, or an ultraviolet source of radiation and corresponding detector. The optical monitoring system 700 can include a controller (not shown in FIG. 7) that can be coupled to the light emitting source 712 and the detector 714. The controller can be configured to control operation of the light emitting source 712 and/or the detector 714. Signals generated by the detector—for example, signals indicating a position of the plunger 706 based on a detected intensity of reflected light received—can be provided to the controller. The controller can subsequently determine a position and movement of the plunger 706 or any component of the drive system for operating the plunger 706 based on signals generated by the detector 714. The controller can further determine how much liquid drug has been expelled and/or how much liquid drug remains in the drug container 704.

Figure 8:
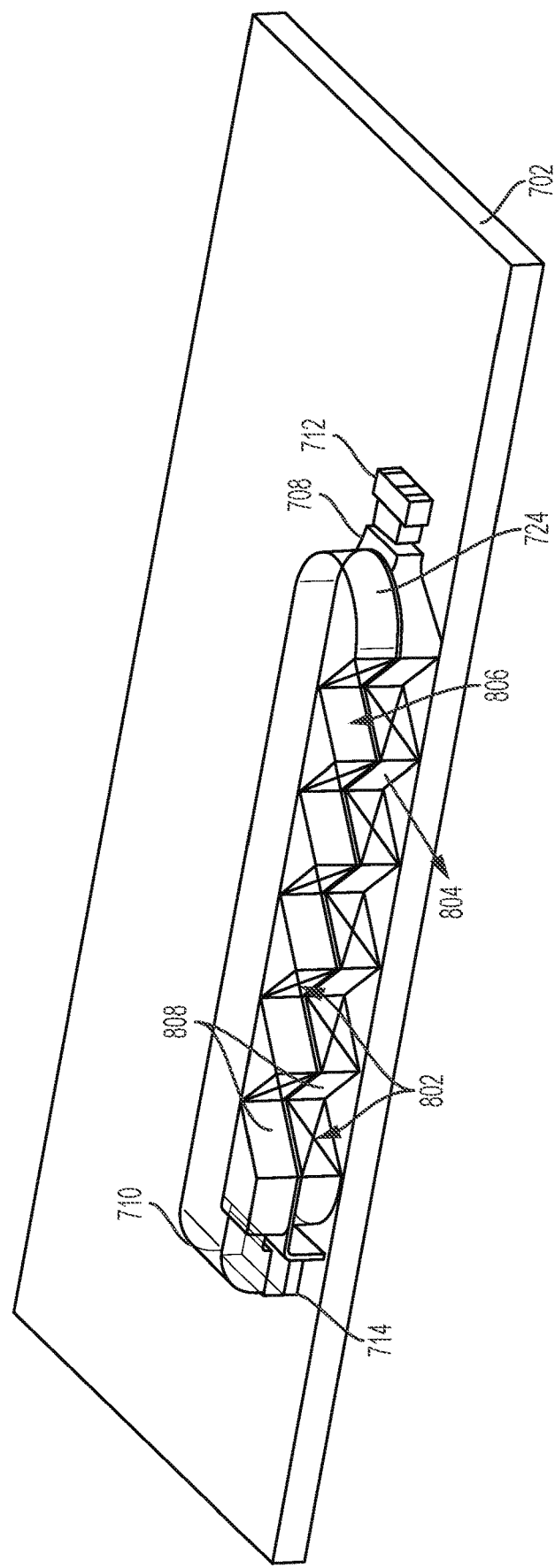
FIG. 8 illustrates an exemplary arrangement of an attenuating light pipe and a non-attenuating light pipe depicted in FIG. 7.

FIG. 8 illustrates an exemplary arrangement of the attenuating light pipe 708 and the non-attenuating light pipe 710 depicted in FIG. 7. As shown in FIG. 8, the attenuating light pipe 708 and the non-attenuating light pipe 710 can each include windows 808 for emitting light and receiving light, respectively. Certain windows 808 can be covered with an anti-reflective (e.g., non-transmissive) coating 802 such that no light is emitted or received through a window 808 coated with anti-reflective coating 802.

For the attenuating light pipe 708, the anti-reflective coating 802 can be placed on the windows 808 that are oriented at a first angle relative to the light emitted by the light emitting source 712. As such, as shown in FIG. 8, light can only be passed through those windows 808 that are not covered by the anti-reflective coating 802. The windows 808 of the attenuating light pipe 708 that can pass light can be oriented at a second angle that is orthogonal to the first angle as shown. Indicator 804 shows an exemplary direction of light that can be emitted or passed from the attenuating light pipe 708.

For the non-attenuating light pipe 710, the anti-reflective coating 802 can be placed on windows 808 that are orthogonal to the windows 808 of the attenuating light pipe 708 that are coated with the anti-reflective coating 802 as shown in FIG. 8. Accordingly, the non-attenuating light pipe 710 can receive light through windows 808 that are orthogonal to the windows 808 of the attenuating light pipe 708 that can emit light, but are not so limited. That is, the windows 808 of the attenuating light pipe 708 that emit light can be oriented according to any angle with respect to the windows 808 of the non-attenuating light pipe 710. In various embodiments, the windows 808 for emitting and receiving light can be oriented at an obtuse or an acute angle with respect to one another. In general, the angle of orientation can be adjusted to provide a desired effective intensity for the light energy received by the non-attenuating light pipe 710.

Indicator 806 shows an exemplary direction of light that can be received by the non-attenuating light pipe 710. The arrangement of the windows 808 and the coated windows 802 of the attenuating light pipe 708 and the non-attenuating light pipe 710 can ensure that attenuated light emitted by the attenuating light pipe 708 is directed toward the detector 714 after it reflects off the plunger 706. In particular, reflected light from the plunger 706 can pass through an uncoated window 808 of the non-attenuating light pipe 710 and then directed toward the detector 714.

Figure 9:
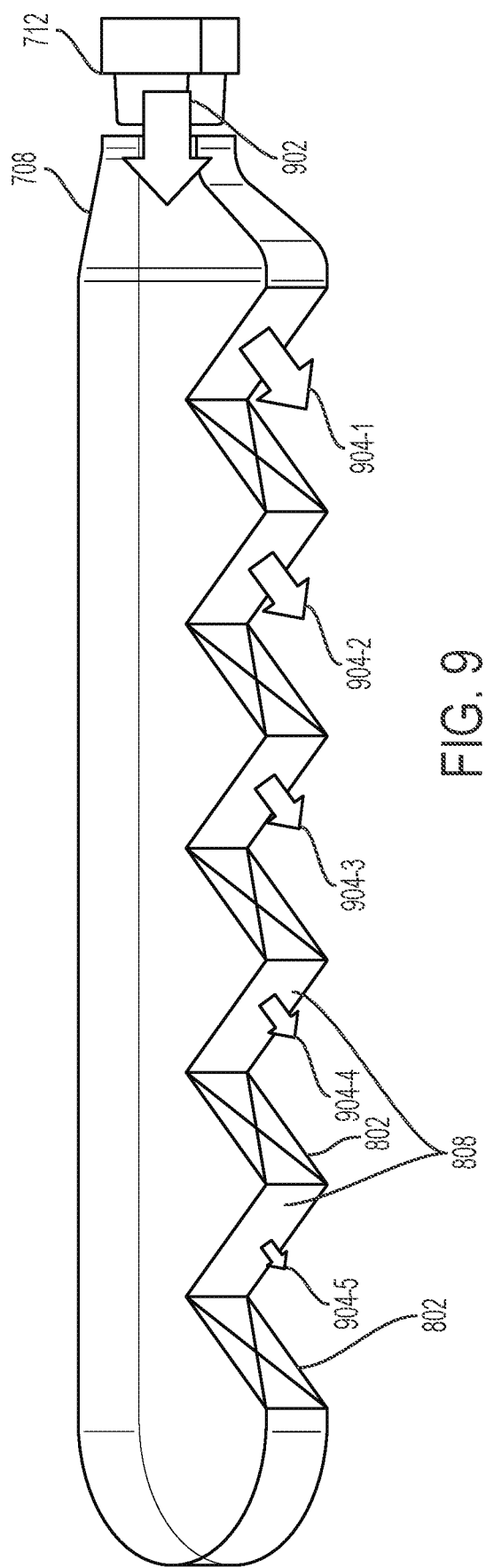
FIG. 9 illustrates an exemplary arrangement of the attenuating light pipe depicted in FIGS. 7 and 8.

FIG. 9 illustrates an exemplary arrangement of the attenuating light pipe 708 depicted in FIGS. 7 and 8. Emitted light 902 represents the light emitted from the light emitting source 712 and its intensity (e.g., as indicated by a size of the corresponding arrow representing the light). The emitted light 902 can travel down the attenuating light pipe 708 and can exit from windows 808 that are not covered with coating 802. Emitted light 904-1 through 904-5 represents the light that passes through each corresponding window 808 and its intensity. The attenuating light pipe 708 can be configured to have an attenuation profile that attenuates the emitted light 902 more the further the light is from the light emitting source 712 (e.g., compare the relatively higher intensity of the emitted light 904-1 to the relatively lower intensity emitted light 904-5). Accordingly, the intensity of the light that is emitted from the windows 808 that are closer to the light emitting source 712—such as, emitted light 904-1—can be greater than the intensity of the light that is emitted from the windows 808 that are further from the light emitting source 712—such as, emitted light 904-5.

The different levels of intensities of the emitted light 904-1 through 904-5 can be reflected off the reflective portion 722 of the plunger 706 as the plunger 706 advances into the drug container 704 and moves along the length of the attenuating light pipe 708 as described above. As such, the intensity of the light received by the detector 714 can change (e.g., increase or decrease as the plunger 706 moves further into the drug container 704 depending upon the arrangement of the components of the optical monitoring system 700). The varying intensity of the light received by the detector 714 can be used to determine a position of the plunger 706. For example, the emitted light 904-1, when reflected off of the reflective portion 722 and then received by the non-attenuating light pipe 710 and the detector 714, can indicate a first position of the plunger 706. Correspondingly, emitted light 904-5, when reflected off of the reflective portion 722 and then received by the non-attenuating light pipe 710 and the detector 714, can indicate a second, different position of the plunger 706. In various embodiments, the detector 714 can generate a signal indicative of the intensity of the received light. The signal can be provided to the controller that can then use the signal to determine a position and/or movement of the plunger 706. The fill status of the drug container 704 (e.g., how much liquid drug remains in the drug container 704 or has been expelled) can then be determined.

The attenuating light pipe 708 can be configured to have any attenuation profile. In various embodiments, the attenuating light pipe 708 can be configured to have a linear attenuation profile. The attenuating light pipe 708 can be formed of a material having a homogenous attenuation profile that can scatter and/or absorb light to cause attenuation. In general, as light travels further into the attenuation light pipe 708, more attenuation is provided, thereby causing larger decreases in intensity in the light as it travels further into the attenuating light pipe 708 (e.g., further away from the light source 712). The attenuating light pipe 708 can be made from various types of materials including plastics and can be covered with an attenuation coating or other material. In various embodiments, the attenuating light pipe 708 can be formed from polymethylmethacrylate (PMMA).

Figure 10:
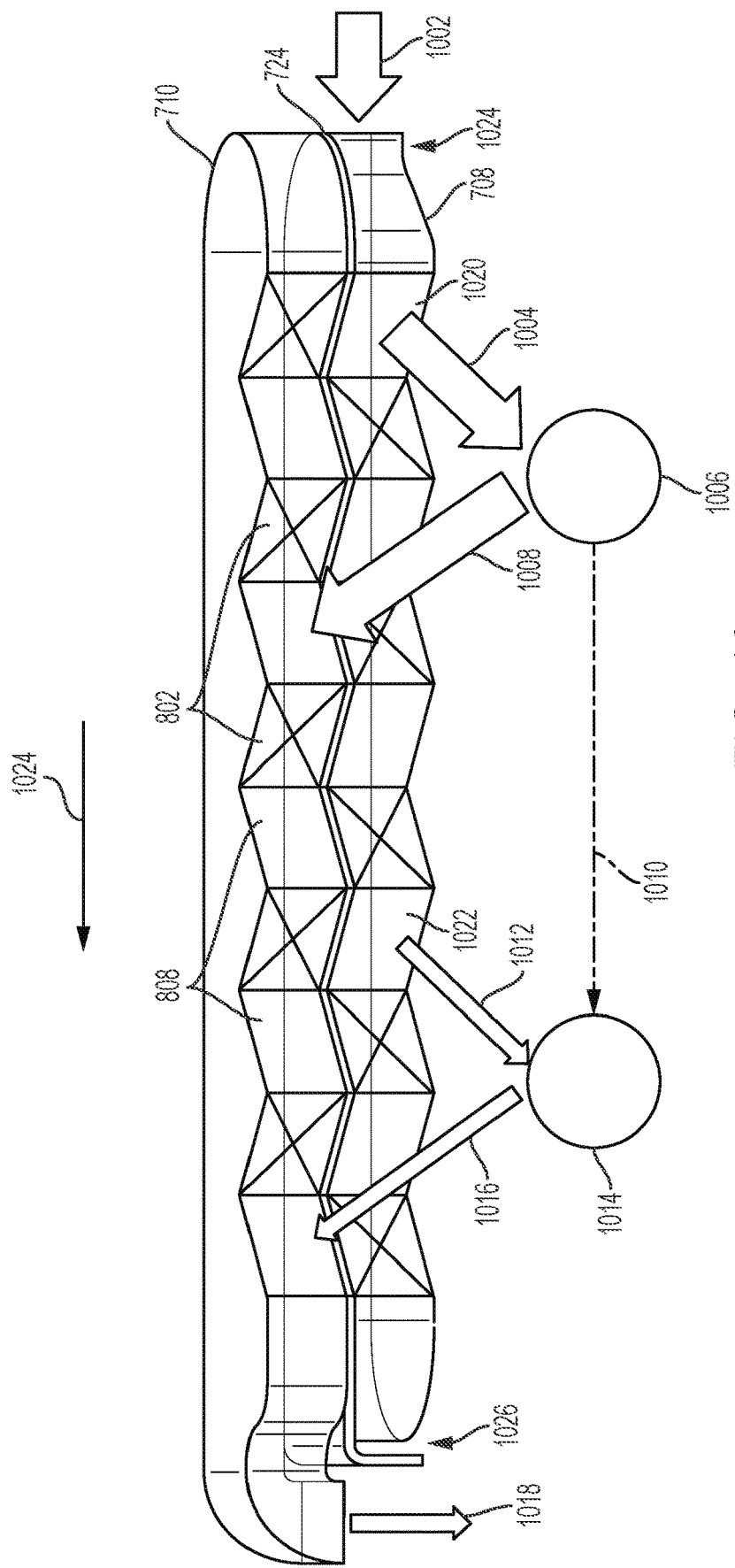
FIG. 10 illustrates an exemplary operation of the optical monitoring system depicted in FIG. 7.

FIG. 10 illustrates an exemplary operation of the optical monitoring system 700. As shown in FIG. 10, the attenuating light pipe 708 is positioned on top of the non-attenuating light pipe 710. The reflector 724 is positioned between the attenuating light pipe 708 and the non-attenuating light pipe 710. A light beam 1002 is shown entering the attenuating light pipe 708. The light beam 1002 can be provided by the light emitting source 712 depicted in FIG. 7. The light beam 1002 can travel along the attenuating light pipe 708 and can exit as an attenuated version of the light beam 1002 from any of the windows 808 that are not coated windows 802. For example, the light beam 1002 can exit a first window 1020 along the attenuated light pipe 708 as a first exit light beam 1004. The first exit light beam 1004 can be an attenuated version of the light beam 1002. The first exit light beam 1004 can be attenuated by a first amount relative to the intensity of the light beam 1002.

The light beam 1002 can further exit a second window 1022 along the attenuated light pipe 708 as a second exit light beam 1012. The second exit light beam 1012 can be also be an attenuated version of the light beam 1002. Indicator 1024 can specify a direction of increasing attenuation by the attenuating light pipe 708. Specifically, the attenuating light pipe 708, as described herein, can attenuate the light beam 1002 more further along the length of the attenuating light pipe 708 relative to an entry point of the light beam 1002. Accordingly, the first exit light beam 1004 can be attenuated less than the second exit light beam 1012. For purposes of explanation, the first exit light beam 1004 is shown to be wider than the second exit light beam 1012 to represent that the second exit light beam 1012 is more attenuated than the first exit light beam 1004. The second exit light beam 1012 can be attenuated by a second amount relative to the intensity of the light beam 1002.

Object 1006 can represent a first position of the plunger 706 (and/or a position of any reflective portion of the plunger 706). As shown in FIG. 10, the first exit light beam 1004 is reflected off the object 1006 as a first reflective light beam 1008. The first reflective light beam 1008 can pass through any of the windows 808 of the non-attenuating light pipe 710 that are not coated windows 802. The first reflective light beam 1008 can then travel through the non-attenuating light pipe 710 and can be provided to the detector 714 depicted in FIG. 7.

Indicator 1010 represents a travel path of the plunger 706. As shown in FIG. 10, the travel path 1010 of the plunger 706 can be substantially parallel to the arrangement of the attenuating and non-attenuating light pipes 708 and 710. Object 1014 can represent a second position of the plunger 706 (and/or a position of any reflective portion of the plunger 706). As shown in FIG. 10, the second exit light beam 1012 is reflected off the object 1014 as a second reflective light beam 1016. The second reflective light beam 1016 can pass through any of the windows 808 of the non-attenuating light pipe 710 that are not coated windows 802. The second reflective light beam 1016 can then travel through the non-attenuating light pipe 710 and can be provided to the detector 714 depicted in FIG. 7.

Light beam 1018 can represent light that exits the non-attenuating light pipe 710 and is provided to the detector 714. The light beam 1018 can be an attenuated version of the light beam 1002. The level of attenuation experienced by the light beam 1018 can be substantially based on the level of attenuation experienced by the initial light beam 1002 from the attenuating light pipe 708, which is then reflected by the plunger 706. For example, the light beam 1018 will experience less attenuation and will be more intense if the plunger 706 is positioned closer to a first end 1024 of the attenuating light pipe 708 in comparison to when the plunger 706 is positioned closer to a second end 1026 of the attenuating light pipe 708. That is, when the position of the plunger 706 can be represented by the object 1006, the intensity of the light beam 1018 will be relatively larger (e.g., due to relatively lower experienced attenuation) since the first reflective light beam 1008 is reflected off of the plunger 706. When the position of the plunger 706 can be represented by the object 1014, the intensity of the light beam 1018 will be relatively smaller (e.g., due to relatively higher experienced attenuation) since the second reflective light beam 1016 is reflected off the plunger 706.

The detector 714 can detect the light beam 1018. As described herein, the detector 714 can measure an intensity of the light beam 1018. For example, the detector 714 can generate a signal based on the measured intensity of the light beam 1018. Signals generated by the detector 714 can be provided to a controller (not shown in FIG. 10). The controller can determine a position of the plunger 706 within the drug container 704 based on the signal provided to the controller by the detector 714. For example, the controller can determine the plunger 706 is positioned closer to the first end 1024 of the attenuating light pipe 708 when the detector 714 generates a signal in response to a relatively more intense light beam 1018. The controller can determine the plunger 706 is positioned closer to the second end 1026 of the attenuating light pipe 708 when the detector 714 generates a signal in response to a relatively less intense light beam 1018. The position of the plunger 706 relative to the drug container 704 can therefore be determined, enabling a determination of how much liquid drug remains in the drug container or how much liquid drug has been expelled from the drug container 704. Further determinations such as a rate of movement of the plunger 706 can also be determined.

Figure 11:
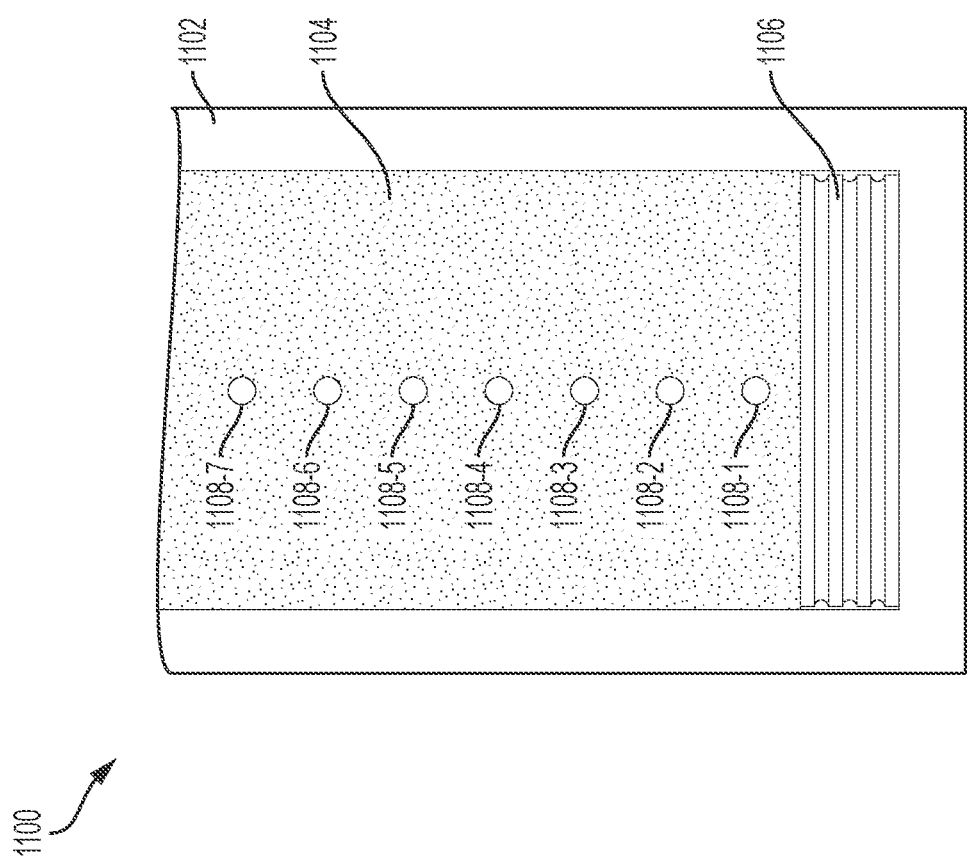
FIG. 11 illustrates an exemplary monitoring system.

FIG. 11 illustrates an exemplary monitoring system 1100. The monitoring system 1100 can include a drug container 1102. A portion of the drug container 1102 is shown in FIG. 11. The drug container 1102 can hold or store a liquid drug 1104. The monitoring system 1100 can further include a plunger 1106 positioned in the drug container 1102. The plunger 1106 can be moved or advanced to expel the liquid drug 1104 from the drug container 1102. The drug container 1102 can represent the drug container 102. The plunger 1106 can be moved to expel the liquid drug 1104 out of either end of the drug container 1102 as will be appreciated by a person having ordinary skill in the art, for example as described above in relation to FIG. 2.

As shown in FIG. 11, the monitoring system 1100 can also include a number of pins 1108. The pins 1108 can be positioned within the drug container 1102. The pins 1108 can be molded into the drug container 1102. The pins 1108 can be made from a conductive material such as a metal. The pins 1108 can be positioned and shaped so as to be flush (aligned) or approximately flush with an inner or interior surface of the drug container 1102. The pins can also be positioned and shaped so as to be flush (aligned) or approximately flush with an outer or outside surface of the drug container 1102.

As shown in FIG. 11, seven (7) pins 1108 are shown as inserted molded into the drug container 1102—pins 1108-1 through 1108-7. Any number of pins 1108 can be positioned in the drug container 1102 and can be arranged in any manner. The liquid drug 1104 stored in the drug container 1102 can provide electrical conductivity between the pins 1108. A controller and/or other circuitry coupled to the pins 1108 (not shown in FIG. 11 for simplicity) can monitor the electrical connectivity of the pins 1108 relative to one another and/or the liquid drug 1106. As the plunger 1106 is moved to expel the liquid drug 1104 from the drug container 1102, a portion of the pins 1108 can become electrically decoupled from the other pins 1108 and/or the liquid drug 1104. The controller can monitor the changing status of the electrical connectivity of the pins 1108 to determine a position and/or movement of the plunger 1106. In this way, the monitoring system 1100 can determine a fill status of the drug container 1102 and/or other information regarding dosing rate, an amount of the liquid drug 1104 expelled from the drug container 1102, and/or a rate of movement of the plunger 1106. As shown in FIG. 11, all of the pins 1108-1 through 1108-7 can be electrically coupled to one another as each pin 1108 is coupled to the liquid drug 1104.

Figure 12:
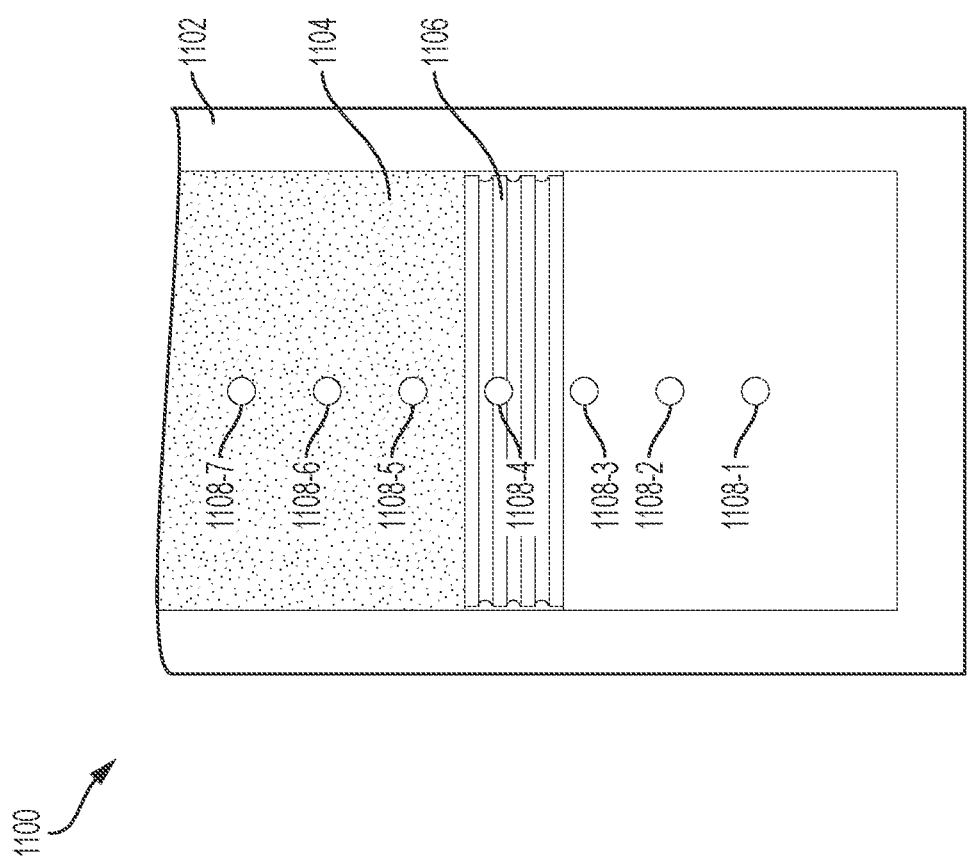
FIG. 12 illustrates operation of the exemplary monitoring system of FIG. 11.

FIG. 12 illustrates the monitoring system 1100 after a portion of the liquid drug 1104 has been expelled from the drug container 1102. As shown in FIG. 12, the plunger 1106 has moved past the pins 1108-1 through 1108-3 and is positioned adjacent to the pin 1108-4. The pins 1108-1 through 1108-4 are no longer coupled to the liquid drug 1104. Consequently, the pins 1108-1 through 1108-4 are no longer electrically connected or coupled to any other pin 1108. The controller coupled to the pins 1108 can determine which pins 1108 are electrically coupled together (e.g., and/or coupled to the liquid drug 1104) and can determine a position of the plunger 1104. For example, as shown in FIG. 12, the controller can determine that a front surface of the plunger 1106 (e.g., a surface of the plunger in contact with the liquid drug 1104) can be positioned between the pin 1108-4 and the pin 1108-5. The controller can also determine that pins 1108-5 through 1108-7 are electrically connected and coupled to the liquid drug 1104. Accordingly, the monitoring system 1100 allows an approximate position of the plunger 1106 to be determined. In turn, the monitoring system 110 can determine how much of the liquid drug 1104 remains in the drug container 1102 and how much liquid drug 1104 has been expelled from the drug container 1102.

As mentioned above, the monitoring system 1100 can use number of pins 1108. The pins 1108 can be spaced apart from one another by a fixed distance but are not so limited. As will be appreciated by a person of ordinary skill in the art, the monitoring system 1100 can use more pins 1108 to provide a better or more accurate approximation as to the location of the plunger 1106 within the drug container (and therefore a better or more accurate approximation of the fill status of the drug container 1102).

Figure 13:
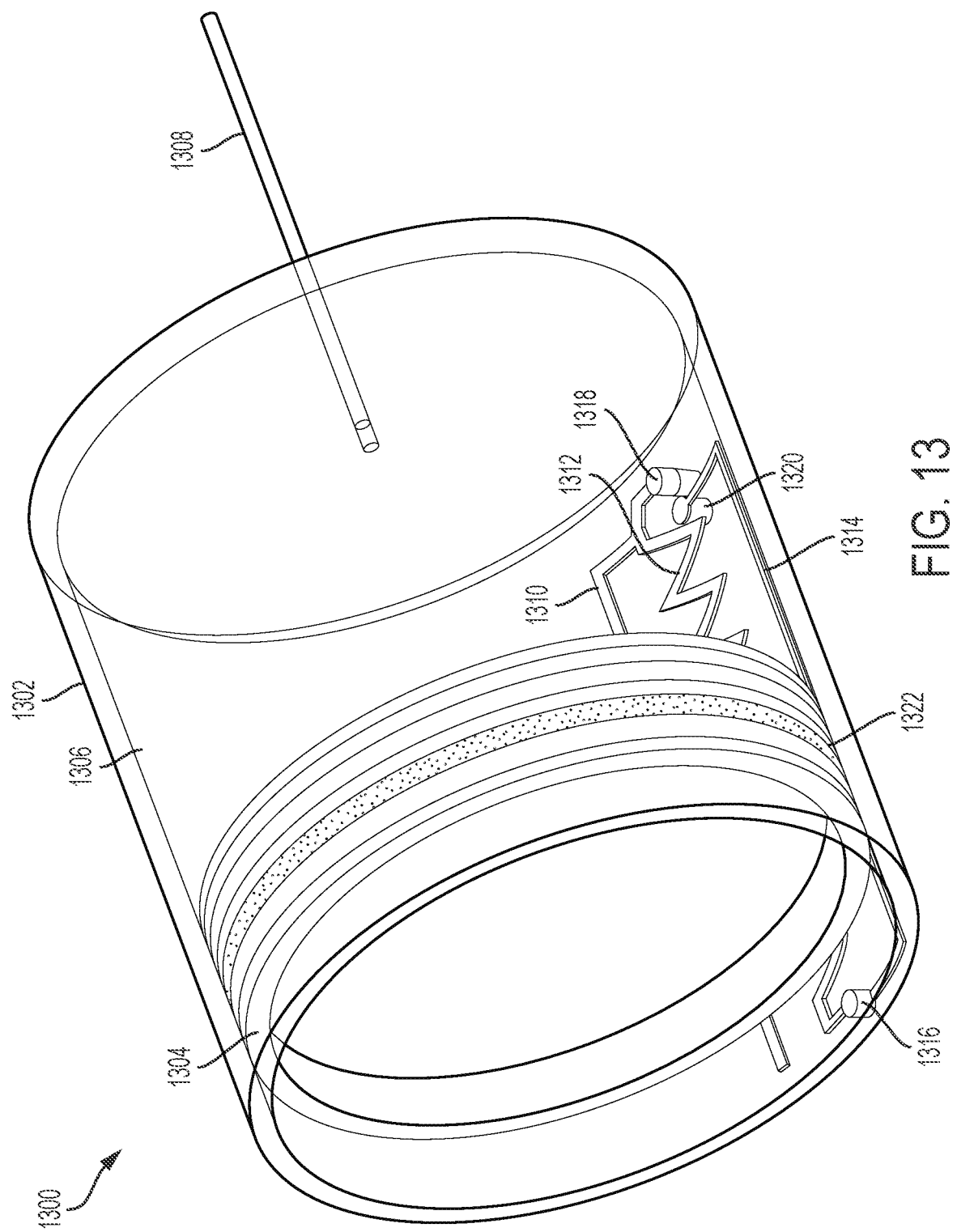
FIG. 13 illustrates a second exemplary monitoring system.

FIG. 13 illustrates a second exemplary monitoring system 1300. The monitoring system 1300 can include a drug container 1302. The drug container 1302 can hold or store a liquid drug 1306. The monitoring system 1300 can further include a plunger 1304 positioned in the drug container 1302. The plunger 1304 can be moved or advanced to expel the liquid drug 1306 from the drug container 1302. The drug container 1302 can represent the drug container 102. The plunger 1304 can be moved to expel the liquid drug 1306 out of the drug container 1302 through a fluid path 1308 (e.g., by moving toward the fluid path 1308). As will be appreciated by a person of ordinary skill in the art, the plunger 1302 and the fluid path 1308 can be arranged to enable the liquid drug 1306 to be expelled through the plunger 1304 (e.g., through an opposite end of the drug container 1302 from what is shown in FIG. 13), for example as described above in relation to FIG. 2.

As shown in FIG. 13, the monitoring system 1300 can further include a first conductive component or trace 1310, a second conductive component or trace 1312, a third conductive component or trace 1314, a first conductive pin 1316, a second conductive pin 1318, and a third conductive pin 1320. The traces 1310, 1312, and 1314 and the pins 1316, 1318, and 1320 can be formed of an electrically conductive material. A conductive ring or wiper 1322 can be positioned around the plunger 1034. The ring 1322 can be formed of an electrically conductive material.

The first trace 1310 can be coupled to the pin 1318. The first trace 1310 can be positioned inside of the drug container 1302. The first trace 1310 can be coupled to an inner surface of the drug container 1302. The first trace 1310 can extend along a substantial portion of a longitudinal length of the drug container 1302.

The second trace 1312 can be coupled between the pin 1318 and the pin 1316. The second trace can also be coupled to the inner surface of the drug container 1302. The second trace can also extend along a substantial portion of the longitudinal length of the drug container 1302. The second trace 1312 can be formed of a material having an increasing resistance (e.g., a linearly increasing resistance).

The third trace 1314 can be coupled to the pin 1316 and the pin 1320. The third trace 1314 can be positioned outside of the drug container 1302. The third trace 1314 can be coupled to an outer surface of the drug container 1302. The third trace 1314 can extend along a substantial portion of the longitudinal length of the drug container 1302.

A portion of the pin 1318 can extend into the drug container 1302 and a portion of the pin 1318 can extend outside of the drug container 1302. A portion of the pin 1316 can also extend into the drug container 1302 and a portion of the pin 1316 can also extend outside of the drug container 1302. The pin 1320 can be positioned on the outside of the drug container 1302. The portions of the pins 1318 and 1316 that extend into the drug container 102 and the traces 1310 and 1312 can be in contact with the liquid drug 1306 stored in the drug container 1302. The trace 1314 and the pin 1320 can be positioned so as to not be in contact with the liquid drug 1306.

The pins 1318 and 1320 can be coupled to one or more output circuits and/or a controller (not shown in FIG. 13 for simplicity). The traces 1310, 1312, and 1314, and the pins 1316, 1318, and 1320 can form a variable resistive network. The variable resistive network can be used to determine a position of the plunger 1306 within the drug container 1302, enabling a fill status of the drug container 1302 to be determined. As the plunger 1304 moves from an initial position (e.g., at or near a far end of the drug container 1302) toward the fluid path 1308, the ring 1322 electrically couples (e.g., shorts) the trace 1310 to the trace 1312 along different corresponding portions of the traces 1310 and 1312. Coupling the trace 1310 to the trace 1312 completes a circuit. Based on the variable resistivity of the trace 1312, the coupling of the trace 1310 to the trace 1312 completes a circuit having different resistance values based on the location of the plunger 1304.

For example, when the ring 1322 couples the trace 1310 to the trace 1312 at a far end of the drug container 1302 (e.g., in close proximity to the pin 1316), the completed circuit can have a relatively lower resistance, as only a relatively small portion of the trace 1312 is included in the completed circuit (due to the shorting of the traces 1310 and 1312 by the ring 1322). When the ring 1322 couples the trace 1310 to the trace 1312 at a near end of the drug container 1302 (e.g., in closer proximity to the fluid path 1308 and/or the pin 1318), the completed circuit can have a relatively higher resistance, as a relatively larger portion of the trace 1312 is included in the completed circuit. Inclusion of a larger portion of the trace 1312 in the completed circuit results in the completed circuit having relatively higher resistance values, such that movement of the plunger 1304 can result in completed circuits of increasing resistance (e.g., linearly increasing resistance). The completed circuit—referenced to the pins 1318 and 1320—can be provided or coupled to the controller or other output circuits. Based on the variable resistance of the completed circuit, the controller can determine a position of the plunger 1304 and therefore a fill status of the drug container 1302.

Figure 14:
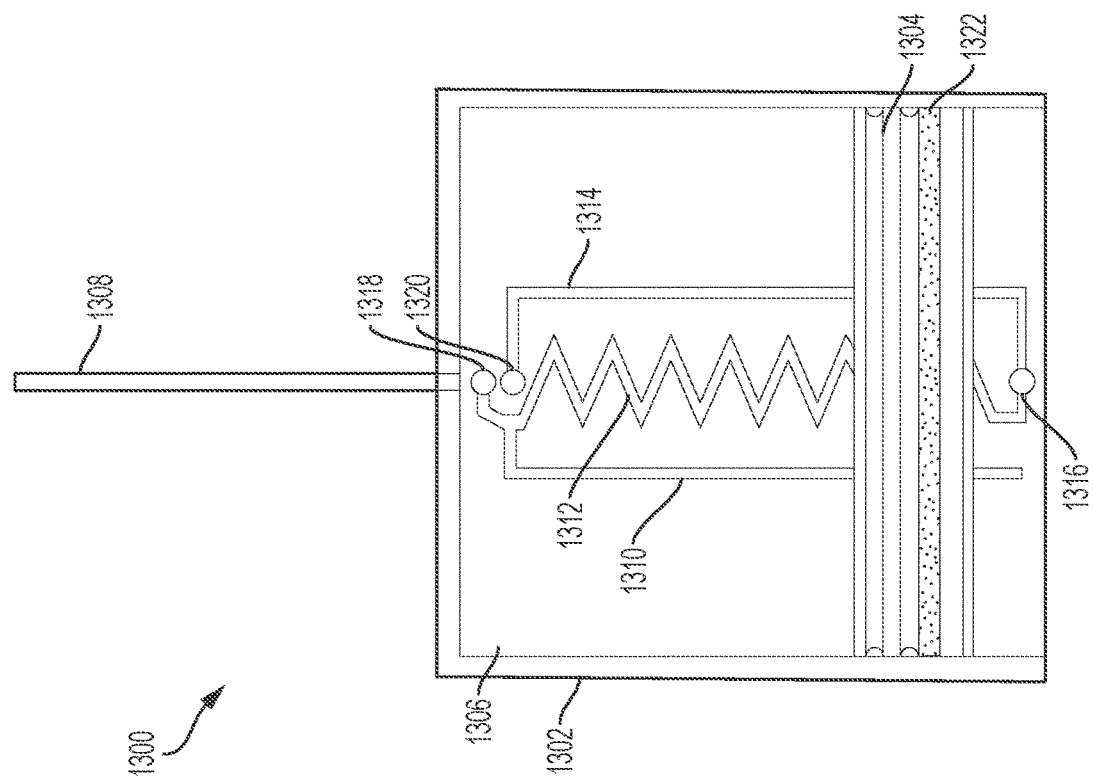
FIG. 14 illustrates a top view of the exemplary monitoring system of FIG. 13.

FIG. 14 illustrates a top view of the monitoring system 1300 depicted in FIG. 13. The arrangement of the traces 1310, 1312, and 1314 along the length of the drug container 1302 is shown. Further, the electrical coupling of the trace 1310 and the trace 1312 by the ring 1322 is illustrated. The circuit completed by the ring 1322 includes larger portions of the trace 1312 as the plunger 1304 moves closer to the fluid path 1308. Accordingly, a controller coupled to the output pins 1318 and 1320 can determine the position of the plunger 1304 based on the variable (e.g., increasing) resistance of the completed circuit.

Figure 15:
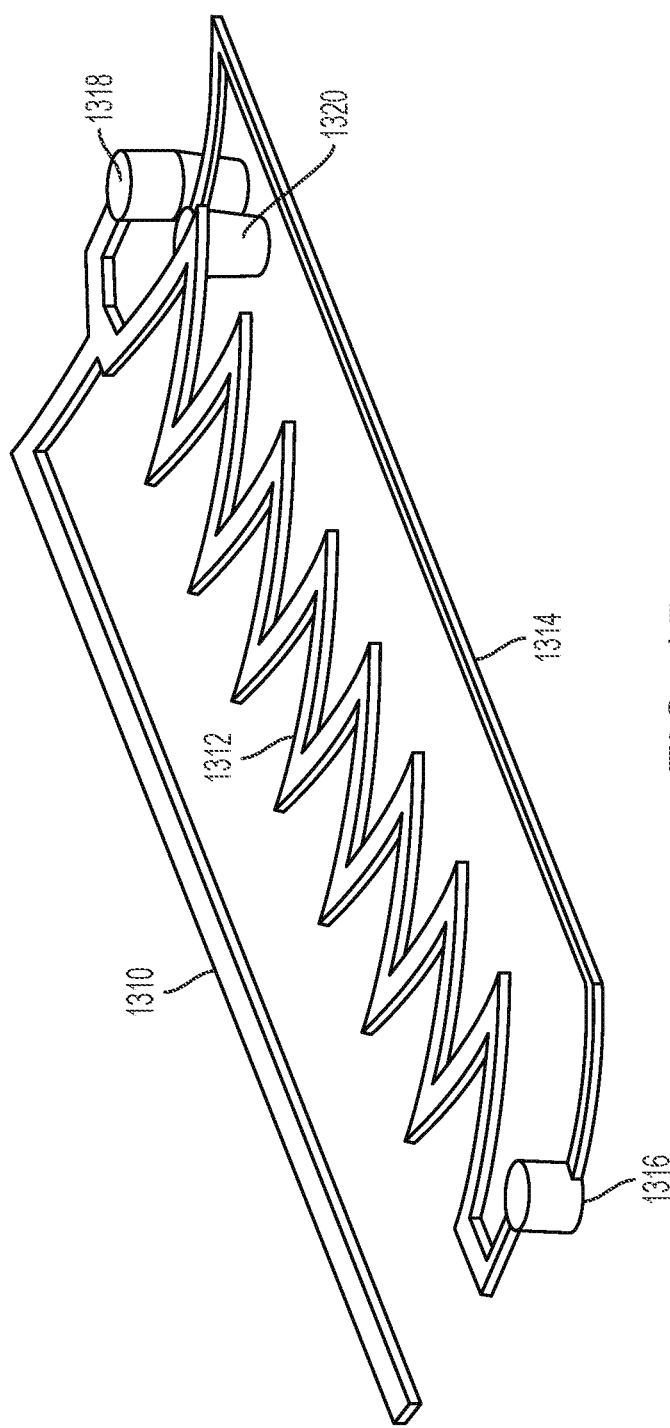
FIG. 15 illustrates a portion of the exemplary monitoring system of FIG. 13.

FIG. 15 illustrates a portion of the monitoring system 1300. Specifically, FIG. 15 illustrates the traces 1310, 1312, and 1314 and the pins 1316, 1318, and 1320. These components can be considered to form a variable resistive network as described above (or a portion of a potentiometer as will be appreciated by a person of ordinary skill in the art). The trace 1312 is shown to have a zigzag shape but is not so limited. In various embodiments, the trace 1312 can be a form a substantially straight trace.

As described herein, systems and methods for monitoring an operational state and/or fill status of a drug container have been provided. Each of the monitoring systems described herein can be combined with any other described monitoring system. The described monitoring systems can be coupled to a user interface device. For example, a controller of the monitoring systems can be coupled to a remote user interface device (e.g., a mobile device) and can provide a patient or user with notifications regarding a fill status of a drug container. In various embodiments, the notification can alert a user to an amount of liquid drug expelled and/or remaining. In various embodiments, the notification can alert a user to when a desired dose of liquid drug has been provided to a patient and/or when the drug container is empty. In various embodiments, the notification can indicate a dosing rate or flow rate of the liquid drug being delivered to the patient. Notifications to the patient can include audible notifications, visual notifications, and/or vibrational notifications. In various embodiments, any described controller can be considered to be a part of any of the described sensors or can be considered to be a separate component of the monitoring systems described herein. In various embodiments, the monitoring systems can associate plunger position with a time stamp such that flow rates, dosing rate, and/or a dosing profile for delivery of a liquid drug to the patient can be determined. In various embodiments, the monitoring systems described herein can be implemented in a wearable drug delivery device.

The following examples pertain to further embodiments:

Example 1 is an apparatus comprising a drug container configured to hold a liquid drug, a plunger positioned in the drug container, a drive system coupled to the plunger, the drive system configured to advance the plunger to expel a portion of the liquid drug from the drug container for delivery to a patient, and one or more sensors positioned adjacent to the drug container, the one or more sensors configured to detect a position of the plunger within the drug container.

Example 2 is an extension of Example 1 or any other example disclosed herein, further comprising a controller coupled to the one or more sensors.

Example 3 is an extension of Example 2 or any other example disclosed herein, wherein the controller is configured to determine an amount of the liquid drug remaining in the drug container based on the detected position of the plunger.

Example 4 is an extension of Example 2 or any other example disclosed herein, wherein the controller is configured to determine the portion of the liquid drug expelled from the drug container based on the detected position of the plunger.

Example 5 is an extension of Example 2 or any other example disclosed herein, wherein the controller is configured to determine a dosing rate of the portion of the liquid drug expelled from the drug container based on the detected position of the plunger.

Example 6 is an extension of Example 2 or any other example disclosed herein, wherein the controller is configured to determine when a desired dose of the liquid drug has been provided to the patient based on the detected position of the plunger.

Example 7 is an extension of Example 2 or any other example disclosed herein, wherein the controller is configured to provide a notification to the patient indicating a fill status of the drug container based on the detected position of the plunger.

Example 8 is an extension of Example 7 or any other example disclosed herein, wherein the notification indicates a desired dose of the liquid drug has been provided to the patient.

Example 9 is an extension of Example 7 or any other example disclosed herein, wherein the notification comprises at least one of an audible notification, a visual notification, and a vibrational notification.

Example 10 is an extension of Example 2 or any other example disclosed herein, wherein the one or more sensors are configured to detect a position of a component of the drive system within the drug container.

Example 11 is an extension of Example 10 or any other example disclosed herein, wherein the component of the drive system comprises one or more spherical elements.

Example 12 is an extension of Example 11 or any other example disclosed herein, wherein the component of the drive system comprises a drive spring.

Example 13 is an extension of Example 12 or any other example disclosed herein, wherein each of the one or more sensors comprise a Hall effect sensor.

Example 14 is an extension of Example 13 or any other example disclosed herein, wherein each Hall effect sensor is configured to count a number of spherical elements that pass the Hall effect sensor.

Example 15 is an extension of Example 13 or any other example disclosed herein, wherein the one or more Hall effect sensors detect an end of a stroke of the plunger.

Example 16 is an extension of Example 13 or any other example disclosed herein, wherein a first Hall effect sensor is positioned adjacent to a first end of the drug container and a second Hall effect sensor is positioned adjacent to a second, opposite end of the drug container.

Example 17 is an extension of Example 12 or any other example disclosed herein, wherein each of the one or more sensors comprise an optical sensor.

Example 18 is an extension of Example 17 or any other example disclosed herein, further comprising one or more light sources, each light source corresponding to one of the one or more optical sensors.

Example 19 is an extension of Example 18 or any other example disclosed herein, wherein each light source is configured to emit light toward the corresponding optical sensor and wherein each optical sensor is configured to receive the corresponding light.

Example 20 is an extension of Example 19 or any other example disclosed herein, wherein each optical sensor is configured to detect when at least one of the plunger and the spherical elements interrupts reception of the corresponding light beam.

Example 21 is a method comprising positioning a plunger in a drug container holding a liquid drug, advancing the plunger further into the drug container using a drive system to expel the liquid drug from the drug container, delivering the expelled liquid drug to a patient, and detecting a position of the plunger within the drug container using one or more sensors positioned adjacent to the drug container.

Example 22 is an extension of Example 21 or any other example disclosed herein, further comprising determining an amount of the liquid drug remaining in the drug container based on the detected position of the plunger.

Example 23 is an extension of Example 21 or any other example disclosed herein, further comprising determining an amount of the liquid drug expelled from the drug container based on the detected position of the plunger.

Example 24 is an extension of Example 21 or any other example disclosed herein, further comprising determining a dosing rate of the liquid drug expelled from the drug container based on the detected position of the plunger.

Example 25 is an extension of Example 21 or any other example disclosed herein, further comprising determining when a desired dose of the liquid drug has been provided to the patient based on the detected position of the plunger.

Example 26 is an extension of Example 21 or any other example disclosed herein, further comprising providing a notification to the patient indicating a fill status of the drug container based on the detected position of the plunger.

Example 27 is an extension of Example 26 or any other example disclosed herein, wherein the notification indicates a desired dose of the liquid drug has been provided to the patient.

Example 28 is an extension of Example 26 or any other example disclosed herein, wherein the notification comprises at least one of an audible notification, a visual notification, or a vibrational notification.

Example 29 is an extension of Example 21 or any other example disclosed herein, further comprising detecting a position of a component of the drive system within the drug container.

Example 30 is an extension of Example 29 or any other example disclosed herein, further comprising detecting the position of the plunger or the component of the drive system based on measuring a varying magnetic field, wherein each of the one or more sensors are Hall effect sensors.

Example 31 is an extension of Example 21 or any other example disclosed herein, further comprising detecting the position of the plunger or the component of the drive system based on detecting an interruption in receiving an emitted light, wherein each of the one or more sensors are optical sensors.

The following examples pertain to further additional embodiments:

Example 1 is an apparatus comprising a drug container configured to hold a liquid drug, a plunger positioned in the drug container, a needle conduit coupled to the plunger, a drive system coupled to the plunger, the drive system configured to advance the plunger to expel a portion of the liquid drug from the drug container through the needle conduit for delivery to a patient, and one or more sensors coupled to the needle conduit and configured to detect a position of the plunger within the drug container based on corresponding advancement of the needle conduit.

Example 2 is an extension of Example 1 or any other example disclosed herein, wherein the needle conduit comprises one or more conductive regions and one or more non-conductive regions.

Example 3 is an extension of Example 2 or any other example disclosed herein, wherein the one or more conductive regions and the one or more non-conductive regions are arranged in a predetermined manner.

Example 4 is an extension of Example 3 or any other example disclosed herein, wherein each of the one or more conductive regions are of a predetermined size.

Example 5 is an extension of Example 3 or any other example disclosed herein, wherein each of the one or more non-conductive regions are of a predetermined size.

Example 6 is an extension of Example 3 or any other example disclosed herein, wherein each of the one or more sensors are electrical sensors.

Example 7 is an extension of Example 6 or any other example disclosed herein, wherein the one or more sensors detect the one or more conductive regions and the one or more non-conductive regions of the needle conduit as the needle conduit advances in response to advancement of the plunger by the drive system.

Example 8 is an extension of Example 7 or any other example disclosed herein, further comprising a controller coupled to the one or more electrical sensors.

Example 9 is an extension of Example 8 or any other example disclosed herein, wherein the controller is configured to determine the position of the plunger based on electrical signals provided by the one or more electrical sensors.

Example 10 is an extension of Example 9 or any other example disclosed herein, wherein the controller is configured to determine an amount of the liquid drug remaining in the drug container based on the detected position of the plunger.

Example 11 is an extension of Example 9 or any other example disclosed herein, wherein the controller is configured to determine the portion of the liquid drug expelled from the drug container based on the detected position of the plunger.

Example 12 is an extension of Example 9 or any other example disclosed herein, wherein the controller is configured to determine a dosing rate of the liquid drug expelled from the drug container based on the detected position of the plunger.

Example 13 is an extension of Example 9 or any other example disclosed herein, wherein the controller is configured to determine when a desired dose of the liquid drug has been provided to the patient based on the detected position of the plunger.

Example 14 is a method comprising positioning a plunger in a drug container configured to hold a liquid drug, advancing the plunger further into the drug container to expel the liquid drug from the drug container through a needle conduit coupled to the plunger, delivering the expelled liquid drug to a patient, and determining a position of the plunger using one or more sensors coupled to the needle conduit.

Example 15 is an extension of Example 14 or any other example disclosed herein, further comprising determining an amount of the liquid drug remaining in the drug container based on the detected position of the plunger.

Example 16 is an extension of Example 14 or any other example disclosed herein, further comprising determining an amount of the liquid drug expelled from the drug container based on the detected position of the plunger.

Example 17 is an extension of Example 14 or any other example disclosed herein, further comprising determining a dosing rate of the liquid drug based on the detected position of the plunger.

Example 18 is an extension of Example 14 or any other example disclosed herein, further comprising determining when a desired dose of the liquid drug has been provided to the patient based on the detected position of the plunger.

Example 19 is an extension of Example 14 or any other example disclosed herein, further comprising providing a notification to the patient indicating the detected position of the plunger.

Example 20 is an extension of Example 19 or any other example disclosed herein, wherein the notification indicates a desired dose of the liquid drug has been provided to the patient.

Example 21 is an extension of Example 14 or any other example disclosed herein, further comprising detecting one or more conductive regions of the needle conduit using the one or more sensors.

Example 22 is an extension of Example 21 or any other example disclosed herein, further comprising detecting one or more non-conductive regions of the needle conduit using the one or more sensors.

Example 23 is an extension of Example 22 or any other example disclosed herein, wherein determining the position of the plunger comprises detecting the one or more conductive regions of the needle conduit and detecting the one or more non-conductive regions of the needle conduit.

Example 24 is an extension of Example 22 or any other example disclosed herein, wherein the one or more sensors are electrical sensors.

The following examples pertain to further additional embodiments:

Example 1 is an apparatus comprising a drug container configured to store a liquid drug, a plunger positioned in the drug container, a drive system coupled to the plunger, the drive system configured to advance the plunger to expel a portion of the liquid drug from the drug container for delivery to a patient, and an optical monitoring system configured to determine a position of the plunger within the drug container.

Example 2 is an extension of Example 1 or any other example disclosed herein, wherein the optical monitoring system is configured to determine a fill status of the drug container based on the determined position of the plunger.

Example 3 is an extension of Example 2 or any other example disclosed herein, wherein a portion of the drug container is transparent.

Example 4 is an extension of Example 3 or any other example disclosed herein, wherein the plunger comprises a reflective portion.

Example 5 is an extension of Example 4 or any other example disclosed herein, wherein the reflective portion is a reflective O-ring.

Example 6 is an extension of Example 5 or any other example disclosed herein, wherein the reflective O-ring is positioned on a head of the plunger.

Example 7 is an extension of Example 4 or any other example disclosed herein, wherein the optical monitoring system comprises a light source.

Example 8 is an extension of Example 7 or any other example disclosed herein, wherein the light source is a light emitting diode (LED).

Example 9 is an extension of Example 7 or any other example disclosed herein, wherein the optical monitoring system comprises an attenuating light pipe coupled to the light source.

Example 10 is an extension of Example 9 or any other example disclosed herein, wherein the optical monitoring system comprises a non-attenuating light pipe.

Example 11 is an extension of Example 10 or any other example disclosed herein, wherein the optical monitoring system comprises a detector coupled to the non-attenuating light pipe.

Example 12 is an extension of Example 11 or any other example disclosed herein, wherein the detector is a photodiode.

Example 13 is an extension of Example 11 or any other example disclosed herein, wherein the attenuating light pipe is positioned over the non-attenuating light pipe.

Example 14 is an extension of Example 13 or any other example disclosed herein, wherein the attenuating light pipe and the non-attenuating light pipe are positioned adjacent to the drug container.

Example 15 is an extension of Example 14 or any other example disclosed herein, wherein a reflective component is positioned between the attenuating light pipe and the non-attenuating light pipe.

Example 16 is an extension of Example 15 or any other example disclosed herein, wherein the attenuating light pipe is configured to attenuate light emitted by the light source.

Example 17 is an extension of Example 16 or any other example disclosed herein, wherein the attenuating light pipe is configured to attenuate the light emitted by the light source according to an attenuation profile.

Example 18 is an extension of Example 17 or any other example disclosed herein, wherein the attenuation profile is linear.

Example 19 is an extension of Example 17 or any other example disclosed herein, wherein the attenuating light pipe is configured to emit an attenuated version of the light emitted by the light source.

Example 20 is an extension of Example 19 or any other example disclosed herein, wherein the light emitted by the attenuating light pipe is attenuated based on a distance traveled by the light emitted by the light source through the attenuating light pipe.

Example 21 is an extension of Example 19 or any other example disclosed herein, wherein the light emitted by the attenuating light pipe is reflected off of the reflective portion of the plunger.

Example 22 is an extension of Example 21 or any other example disclosed herein, wherein the non-attenuating light pipe receives light reflected off of the reflective portion of the plunger.

Example 23 is an extension of Example 22 or any other example disclosed herein, wherein the received light is provided to the detector.

Example 24 is an extension of Example 23 or any other example disclosed herein, wherein the detector generates a signal based on the received light.

Example 25 is an extension of Example 24 or any other example disclosed herein, wherein the signal indicates an amount of attenuation of the light emitted by the light source.

Example 26 is an extension of Example 25 or any other example disclosed herein, wherein the signal is provided to a controller coupled to the detector.

Example 27 is an extension of Example 25 or any other example disclosed herein, wherein the controller determines the position of the plunger based on the signal.

Example 28 is a method, comprising providing light from a light source to an attenuating light pipe, attenuating the light according to an attenuation profile of the attenuating light pipe, emitting the attenuated light from the attenuating light pipe, reflecting the attenuated light from a reflective portion of a plunger positioned in a drug container configured to hold a liquid drug, and providing the reflected attenuated light to a detector.

Example 29 is an extension of Example 28 or any other example disclosed herein, further comprising receiving the reflected attenuated light in a non-attenuating light pipe.

Example 30 is an extension of Example 29 or any other example disclosed herein, further comprising generating a signal based on the reflected attenuated light.

Example 31 is an extension of Example 30 or any other example disclosed herein, further comprising indicating an amount of attenuation of the light provided to the attenuating light pipe in the generated signal.

Example 32 is an extension of Example 31 or any other example disclosed herein, further comprising providing the generated signal to a controller.

Example 33 is an extension of Example 32 or any other example disclosed herein, further comprising determining a relative position of the plunger in the drug container based on the generated signal.

Example 34 is an extension of Example 33 or any other example disclosed herein, further comprising determining an amount of the liquid drug expelled from the drug container based on the determined position of the plunger.

Example 35 is an extension of Example 33 or any other example disclosed herein, further comprising determining an amount of the liquid drug remaining in the drug container based on the determined position of the plunger.

Example 36 is an extension of Example 33 or any other example disclosed herein, further comprising determining when a desired dosage of the liquid drug is provided to a patient based on the determined position of the plunger.

Example 37 is an extension of Example 33 or any other example disclosed herein, further comprising notifying the patient of the determined position of the plunger.

Example 38 is an extension of Example 37 or any other example disclosed herein, further comprising notifying the patient by at least one of a visual indication, an audible indication, and a vibrational indication.

The following examples pertain to further additional embodiments:

Example 1 is an apparatus comprising a drug container configured to hold a liquid drug, a plunger positioned in the drug container, a drive system coupled to the plunger, the drive system configured to advance the plunger to expel a portion of the liquid drug from the drug container for delivery to a patient, a plurality of conductive pins positioned in the drug container, and a controller electrically coupled to each of the plurality of conductive pins.

Example 2 is an extension of Example 1 or any other example disclosed herein, wherein an inner surface of the drug container is aligned with a first end surface of each conductive pin.

Example 3 is an extension of Example 2 or any other example disclosed herein, wherein the first end surface of each conductive pin is disposed in an interior of the drug container.

Example 4 is an extension of Example 2 or any other example disclosed herein, wherein an outer surface of the drug container is aligned with a second end surface of each conductive pin.

Example 5 is an extension of Example 4 or any other example disclosed herein, wherein the second end surface of each conductive pin is disposed in an exterior of the drug container.

Example 6 is an extension of Example 4 or any other example disclosed herein, wherein the second end surface of each conductive pin is electrically coupled to the controller.

Example 7 is an extension of Example 1 or any other example disclosed herein, wherein the plurality of conductive pins are positioned through the drug container.

Example 8 is an extension of Example 1 or any other example disclosed herein, wherein the controller is configured to monitor an electrical connectivity of each of the plurality of conductive pins.

Example 9 is an extension of Example 8 or any other example disclosed herein, wherein the controller is configured to monitor an electrical connectivity of each of the plurality of conductive pins relative to one another.

Example 10 is an extension of Example 8 or any other example disclosed herein, wherein the controller is configured to monitor an electrical connectivity of each of the plurality of conductive pins relative to the liquid drug.

Example 11 is an extension of Example 8 or any other example disclosed herein, wherein the controller is configured to determine a position of the plunger within the drug container based on the monitored electrical connectivity of the plurality of conductive pins.

Example 12 is an extension of Example 11 or any other example disclosed herein, wherein the controller is configured to determine a fill status of the drug container based on the determined position of the plunger.

Example 13 is an extension of Example 1 or any other example disclosed herein, wherein the conductive pins are evenly spaced along the drug container.

Example 14 is a method comprising advancing a plunger positioned in a drug container holding a liquid drug to expel the liquid drug from the drug container, delivering the expelled liquid drug to a patient, and detecting an electrical connectivity between a plurality of conductive pins disposed in the drug container.

Example 15 is an extension of Example 14 or any other example disclosed herein, further comprising determining a position of the plunger within the drug container based on the determined electrical connectivity between the plurality of conductive pins.

The following examples pertain to further additional embodiments:

Example 1 is an apparatus comprising a drug container configured to hold a liquid drug, a plunger positioned in the drug container, a drive system coupled to the plunger, the drive system configured to advance the plunger to expel a portion of the liquid drug from the drug container for delivery to a patient, and a variable resistive circuit disposed on an inner surface of the drug container.

Example 2 is an extension of Example 1 or any other example disclosed herein, wherein the variable resistive circuit comprises a first conductive trace positioned on the inner surface of the drug container and coupled to a first conductive pin, a second conductive trace positioned on the inner surface of the drug container and coupled between the first conductive pin and a second conductive pin, and a conductive ring positioned around an outer surface of the plunger adjacent to the inner surface of the drug container, the conductive ring electrically coupling the first conductive trace to the second conductive trace at a first position corresponding to a position of the plunger within the drug container.

Example 3 is an extension of Example 3 or any other example disclosed herein, wherein the second conductive trace is configured to have a linearly increasing resistance.

Example 4 is an extension of Example 3 or any other example disclosed herein, wherein the first conductive pin comprises a first portion disposed inside of the drug container and a second portion disposed outside of the drug container.

Example 5 is an extension of Example 4 or any other example disclosed herein, wherein the second conductive pin comprises a first portion disposed inside of the drug container and a second portion disposed outside of the drug container.

Example 6 is an extension of Example 5 or any other example disclosed herein, wherein the second conductive pin is coupled to a third conductive trace positioned on an outer surface of the drug container.

Example 7 is an extension of Example 6 or any other example disclosed herein, wherein the third conductive trace is coupled to a third conductive pin disposed on the outer surface of the drug container.

Example 8 is an extension of Example 7 or any other example disclosed herein, wherein a controller is electrically coupled to the first and third conductive pins.

Example 9 is an extension of Example 8 or any other example disclosed herein, wherein the controller is configured to monitor a resistance of the variable resistance circuit.

Example 10 is an extension of Example 9 or any other example disclosed herein, wherein the resistance of the variable resistance circuit increases as the plunger is advanced from a first position to a second position to expel the portion of the liquid drug.

Example 11 is an extension of Example 10 or any other example disclosed herein, wherein the controller is configured to determine the position of the plunger based on the monitored resistance of the variable resistance circuit.

Example 12 is an extension of Example 11 or any other example disclosed herein, wherein the controller is configured to determine a fill status of the drug container based on the determined position of the plunger.

Example 13 is a method comprising advancing a plunger positioned in a drug container holding a liquid drug to expel the liquid drug from the drug container, delivering the expelled liquid drug to a patient, and monitoring a resistance of a variable resistance circuit disposed in the drug container to determine a position of the plunger within the drug container.

Example 14 is an extension of Example 13 or any other example disclosed herein, further comprising coupling a first conductive trace of to a second conductive trace to form the variable resistive circuit, the first and second conductive traces disposed on an inner surface of the drug container.

Example 15 is an extension of Example 14 or any other example disclosed herein, wherein coupling further comprises electrically coupling the first and second conductive traces together by a conductive ring positioned around the plunger.

Example 16 is an extension of Example 15 or any other example disclosed herein, further comprising measuring the resistance of the variable resistance circuit.

Example 17 is an extension of Example 16 or any other example disclosed herein, further comprising determining the position of the plunger based on the measured resistance.

Example 18 is an extension of Example 17 or any other example disclosed herein, further comprising determining a fill status of the drug container based on the position of the plunger.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A monitoring system, comprising:
   a plunger wiper coupled to a plunger positioned within a drug container and operable to travel with the plunger inside the drug container;
   a first conductive trace on an interior surface of the drug container;
   a second conductive trace positioned adjacent to the first conductive trace on the interior surface of the drug container, wherein the plunger wiper is formed from an electrically conductive material and is positioned to electrically couple the first conductive trace and the second conductive trace; and
   a controller electrically coupled to the first conductive trace and the second conductive trace, wherein:
      the first conductive trace and the second conductive trace are operable to form a variable resistance network usable by the controller to determine a fill status of the drug container.

2. The monitoring system of claim 1, wherein:
   the first conductive trace and the second conductive trace are operable to contact a liquid drug in the drug container.

3. The monitoring system of claim 2, wherein the first conductive trace and the second conductive trace are spaced apart and are both coupled to a first pin, and the first pin is electrically coupled to the controller.

4. The monitoring system of claim 1, wherein the second conductive trace has a sawtooth configuration.

5. The monitoring system of claim 1, wherein the second conductive trace is formed of a material with a linearly increasing resistance.

6. The monitoring system of claim 1, wherein the controller is operable to:
   detect a resistance value based on a position of the plunger wiper between two conductive pins.

7. A monitoring system, comprising:
   a plunger wiper coupled to a plunger positioned within a drug container and operable to travel with the plunger inside the drug container;
   a first conductive trace on an interior surface of the drug container;
   a second conductive trace positioned adjacent to the first conductive trace on the interior surface of the drug container; and
   a controller electrically coupled to the first conductive trace and the second conductive trace, wherein:
      the first conductive trace and the second conductive trace are operable to form a variable resistance network usable by the controller to determine a fill status of the drug container; and
   wherein the drug container comprises:
      a first conductive output pin coupled to the first conductive trace and a first end of the second conductive trace within the drug container.

8. The monitoring system of claim 1, wherein the drug container further comprises:
   a second conductive pin coupled to a second end of the second conductive trace and to a first end of a third conductive trace, wherein:
      the second conductive pin extends from an exterior of the drug container into an interior of the drug container, and
      the third conductive trace is positioned to be separate from a liquid drug.

9. The monitoring system of claim 8, wherein the drug container further comprises:
   a third conductive pin coupled to a second end of the third conductive trace.

10. A monitoring system, comprising:
    a plunger wiper coupled to a plunger positioned within a drug container and operable to travel with the plunger inside the drug container;
    a first conductive trace on an interior surface of the drug container;
    a second conductive trace positioned adjacent to the first conductive trace on the interior surface of the drug container; and
    a controller electrically coupled to the first conductive trace and the second conductive trace, wherein:
       the first conductive trace and the second conductive trace are operable to form a variable resistance network usable by the controller to determine a fill status of the drug container; and
    wherein the drug container further comprises:
       a first conductive output pin coupled to the first conductive trace and a first end of the second conductive trace within the drug container; and
    wherein the controller is further configured to:
    monitor a resistance value of the variable resistance network, and
    determine a position of the plunger based on the monitored resistance value.

* * * * *